(12) United States Patent
Bab et al.

(10) Patent No.: US 6,190,318 B1
(45) Date of Patent: Feb. 20, 2001

(54) DEVICE AND METHOD FOR THE ULTRASONIC DETECTION OF SMOOTH SURFACE LESIONS ON TOOTH CROWN SURFACES

(75) Inventors: Itai Bab, Karmei Yossef; Osnat Feuerstein, Jerusalem; Vered Vivi Ziv, Mazkeret Batia, all of (IL)

(73) Assignee: Novadent Ltd., Har Hozvim Jerasulam (IL)

(*) Notice: Under 35 U.S.C. 154(b), the term of this patent shall be extended for 0 days.

(21) Appl. No.: 09/089,920

(22) Filed: Jun. 3, 1998

Related U.S. Application Data

(63) Continuation-in-part of application No. 09/089,919, filed on Jun. 3, 1998, now Pat. No. 6,162,177, which is a continuation of application No. PCT/IL97/00388, filed on Nov. 26, 1997.

(30) Foreign Application Priority Data

Nov. 26, 1996 (IL) .......................................................... 119701
Nov. 26, 1997 (WO) ..................................... PCT/IL97/00388

(51) Int. Cl.$^7$ .......................................................... A61B 8/00
(52) U.S. Cl. .............................................................. 600/437
(58) Field of Search ..................................... 600/437, 438, 600/439; 73/629; 128/916

(56) References Cited

U.S. PATENT DOCUMENTS 5,115,813 * 5/1992 Ylander et al. ...................... 600/437
5,874,677 * 2/1999 Bab et al. .............................. 73/629

* cited by examiner

Primary Examiner—Marvin M. Lateef
Assistant Examiner—Maulin Patel
(74) Attorney, Agent, or Firm—Frommer Lawrence & Haug LLP; William S. Frommer

(57) ABSTRACT

A device and method for the detection of smooth surface lesions such as caries and tooth crown surface cracks on a tooth crown surface, the device having an ultrasonic surface wave transmitter/receiver comprising a focused ultrasonic surface waves along a tooth crown surface. Surface lesions encountered by the ultrasonic surface waves produce ultrasonic surface wave reflections which are receivable at the generator/receiver, thus enabling the presence of the lesion, and particularly small lesions, to be detected. The ultrasonic surface wave generator/receiver may comprise a focused transducer, having a focusing element integral therewith or separate therefrom, operatively connected to a wedge-like coupler. Longitudinal ultrasonic waves generated by the transducers are at least partially focused by the focusing element and then imparted onto the tooth surface by the coupler which has a contact surface in contact with the tooth surface being tested. The coupler also enables ultrasonic surface wave reflections to be received by the transducer.

51 Claims, 18 Drawing Sheets

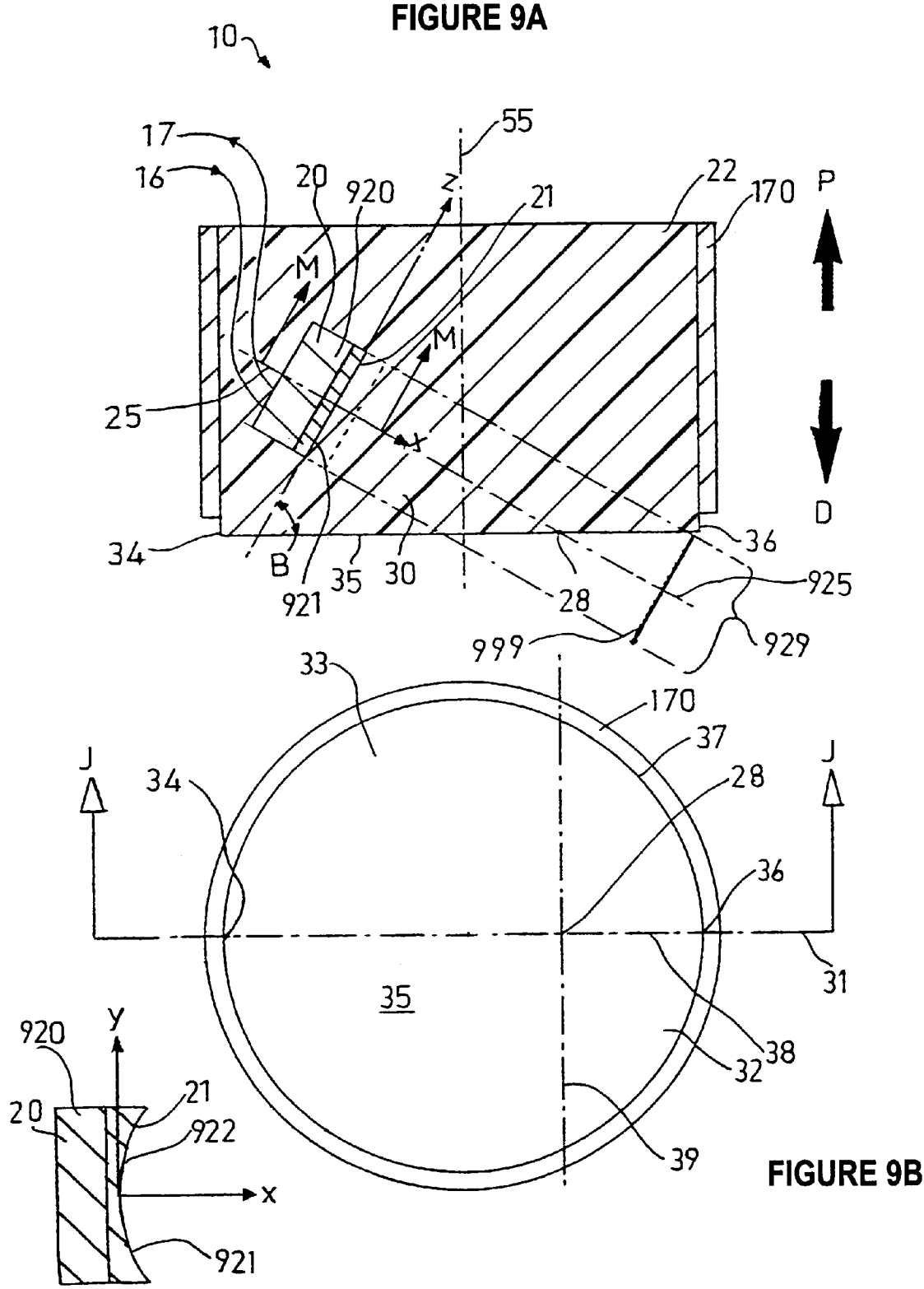

DEVICE AND METHOD FOR THE ULTRASONIC DETECTION OF SMOOTH SURFACE LESIONS ON TOOTH CROWN SURFACES

This is a continuation-in-part of application Ser. No. 09/089,919 filed Jun. 3, 1998, U.S. Pat. No. 6,162,177 being filed concurrently herewith, entitled Device and Method for the Ultrasonic Detection of Smooth Surface Lesions on Tooth Crown Surfaces, which is a continuation of PCT/IL97/00388 filed Nov. 26, 1997.

TECHNICAL FIELD

The present invention relates to the ultrasonic detection of smooth surface lesions on tooth crown surfaces such as enamel caries, dentinal caries and tooth crown surface cracks, for example. In particular, the present invention relates to ultrasonic surface waves imparted on tooth crown surfaces for the detection of these lesions.

BACKGROUND

Dental caries is a disease manifested by local demineralization of the hard tissues of the tooth crown induced by dental plaque. The demineralization process progresses from the outer enamel surface of the crown through the entire thickness of the enamel and into the dentine. Caries lesions of occlusal, buccal and lingual (palatinal) surfaces can be diagnosed by mechanical probing and/or visual inspection. On the other hand, small and medium size lesions of interproximal crown surfaces are hidden by the gingiva and adjacent teeth and have hitherto been identifiable only on radiographs. Although the use of bitewing radiographs is well accepted as an important adjunct in the diagnosis of proximal caries lesions, this method exhibits several weaknesses related to its relative insensitivity and user dependence in terms of technical performance and interpretation [Waggoner W., F. Crall J. J. (1984) Quintessence International 11/1984: 1163–1173]. Furthermore, bitewing radiographs comprise a high proportion of x-rays taken in the dental office. This is in contrast with the current trends in safety standards which support every effort aimed at reducing the exposure to ionizing irradiation. In addition, an alternative technology for the detection of interproximal caries is expected to reduce the environmental pollution and cost associated with the use of x-ray technology.

Caries lesions not adjacent to a dental restoration on a tooth surface site are known as primary caries, while caries lesions in contact with a dental restoration at the tooth surface are known as secondary caries.

The potential of ultrasonic technology for the detection of dental caries, has been proposed in several instances. It has been shown that the hard tissues of the tooth crown, in particular the outer enamel layer, are highly uniform in their sonic properties among different teeth and individuals [Ng S. Y., Payne P. A., Cartledge N. A., Ferguson M. W., (1989), Arch. Oral Biol. 34: 341–345; Barber F. E., Lees S., Lobene R. R., (1969), Arch. Oral Biol. 14: 745–760]. Using a longitudinal ultrasonic irradiation, a specific profile of ultrasonic echoes is obtained from the enamel surface, dentinoenamel junction and pulpodentinal junction. Changes in this profile have been described in instances of demineralization lesions indicating a substantial difference in the sonic conductivity between sound and dimineralized enamel [Ng S. Y., Ferguson M. W. J., Payne P. A., Slater P., (1988), J. Dent 16:201–209; PCT no. WO 95/04506]. These changes result from conversion of the intact enamel to the water rich demineralized material. However, the detection of these lesions is dependent on a direct contact between the ultrasonic probe and the demineralized enamel; such contact cannot be formed in interproximal sites. In addition, echo profiles to longitudinal waves obtained from sound and demineralized tooth crowns are complicated and can be analyzed only by using complex systems.

The present invention relates to a revolutionary approach regarding the use of ultrasonic technology for the detection of primary and secondary dental caries, as well as for the detection of tooth crown surface cracks. Rather than transmitting longitudinal ultrasonic waves into the tooth, as in the prior art, the present invention relates to a probe comprising an ultrasonic surface wave generator that imparts surface ultrasonic waves onto the tooth crown surface, the surface waves then migrating along same. Surface or Rayleigh waves are well known [Cook E. G., Van Valkenburg H. E., (1954) ASTM-Bull 84]. Surface waves migrate uninterruptedly on smooth, flat or curved, contours. Sharp angles, interferences and interfaces present on the surface produce distinct echoes [Krautkrämer H., Ultrasonic Testing of Materials, (1969) Springer-Verlag Berlin Heidelberg New York; pp. 257–271]. The amplitude and shape of these echoes or reflections are dependent on the geometry of such interferences. Thus, the interface between a caries lesion or a tooth crown surface crack and intact enamel may be identified by an echo or reflection of surface ultrasonic waves produced thereat and received by a suitable ultrasonic surface wave receiver, typically unitary with said ultrasonic surface wave generator. Since said reflected surface ultrasonic waves have an amplitude substantially greater than the general level of background noise, the profiles of said waves are relatively simple to analyse. Furthermore, since the ultrasonic probe of the present invention does not require to be placed directly onto the zone of interest on the tooth surface, it is particularly useful for the detection of caries lesions and tooth crown surface cracks in areas such as the interproximal site, hitherto inaccessible with ultrasonic probes or devices of the prior art.

The ultrasonic surface wave generator of the present invention comprises any ultrasonic probe capable of transmitting ultrasonic surface waves along a tooth surface. Such an ultrasonic probe may take the form, for example, of an ultrasonic transducer in which the crystal face of the transducer is substantially at an angle B, substantially different from 0°, to the tested surface, i.e., the tooth crown surface, by virtue of an appropriately designed wedge-like coupler having a contact surface for abutting against the tested surface. Angle B is known as the overall wedge angle of the coupler. In particular, angle B is substantially greater than 0° and less than 90°. The wedge-like coupler enables substantially longitudinal ultrasonic waves generated by the transducer to be imparted on the tooth surface as ultrasonic surface waves when the wedge-like coupler is in contact with a tooth surface via the contact surface of the coupler.

In particular, the ultrasonic waves generated by the transducer may be focused to achieve a higher sensitivity and resolution. The term "focus" is generally understood to mean a concentration of the ultrasonic beam generated by the transducer to a size less in diameter than the diameter of the piezoelectric crystal face. A circular flat piezoelectric crystal or oscillator may have a quasi-focus at the end of the near field, this being a natural one produced by diffraction phenomena. Nonetheless, the term "focus" herein refers rather to the further focusing, either full or partial, of ultrasonic sound waves to an extent substantially greater than is normally achieved from natural diffraction effects obtained with an isolated but similar non-focused transducer having a planar distal face. In particular, the term "focusing" refers to such further focusing arising from at least one focusing element. The focusing element may be optionally integral with the transducer, and may consist, for example, of the distal face of the focused transducer, the distal face being substantially concave with a concavity having an overall curvature substantially sufficient to enable ultrasonic sound waves generated by the focused transducer to be at least partially focused. Alternatively or additionally, the focusing element may constitute separate from the transducer, comprising suitable focusing means such as suitable lenses, mirrors and/or phase plates.

There are two general categories of focusing transducers: spherically focused transducers provide a spot focused beam, while cylindrical focused transducers provide a line focused beam. Spherically focused transducers generally enhance sensitivity as compared with unfocused transducers, and therefore have the advantage of enabling the existence of even small lesions to be detected when incorporated in the probe or device of the present invention. Cylindrical focused transducers generally provide better resolution as compared with unfocused transducers, and thus enable different adjacent lesions to be identified when incorporated in the probe or device of the present invention.

With focused transducers, the overall wedge angle B of the coupler may be conveniently defined as the angle between a plane substantially perpendicular to the principal axis of the focusing element of the focused transducer, and a plane substantially tangential to the contact surface of the coupler at the point of intersection of the principal axis with the contact surface, the wedge angle B being substantially different to 0°, and in particular greater than 0° and less than 90°.

The present invention is defined by the claims, the contents of which are to be read as included within the disclosure of the specification, and will now be described by way of example with reference to the accompanying Figures.

BRIEF DESCRIPTION OF FIGURES

FIG. 1 illustrates the main features of the first embodiment of the probe according to the present invention comprising a planar contact surface.

FIG. 2 illustrates the main features of a second embodiment of the probe according to the present invention, comprising a non-planar contact surface.

FIG. 3 illustrates the main features of the third embodiment of the probe according to the present invention comprising a spot focused transducer incorporating a concave arcuate transducer distal face.

FIG. 4 illustrates the main features of the fourth embodiment of the probe according to the present invention comprising a spot focused transducer incorporating a concave cone-shaped transducer distal face.

FIG. 5 illustrates the main features of the fifth embodiment of the probe according to the present invention comprising a spot focused transducer comprising a plane-concave lens.

FIG. 6 illustrates the main features of the sixth embodiment of the probe according to the present invention comprising a spot focused transducer comprising a concave-cone-shaped converging lens.

FIG. 7 illustrates the main features of the seventh embodiment of the probe according to the present invention comprising a spot focused transducer comprising a hollow converging mirror.

FIG. 8 illustrates the main features of the eighth embodiment of the probe according to the present invention comprising a spot focused transducer comprising a phase plate.

FIG. 9 illustrates the main features of the ninth embodiment of the probe according to the present invention comprising a line focused transducer incorporating a concave cylindrical transducer distal face; FIG. 9(a) is cross sectional view of the embodiment shown in FIG. 9(b) taken along J—J; FIG. 9(b) is a bottom view of this embodiment; FIG. 9(c) is a cross-section of the transducer taken along M—M.

FIG. 10 illustrates the main features of the tenth embodiment of the probe according to the present invention.

DESCRIPTION

Figure 1A:
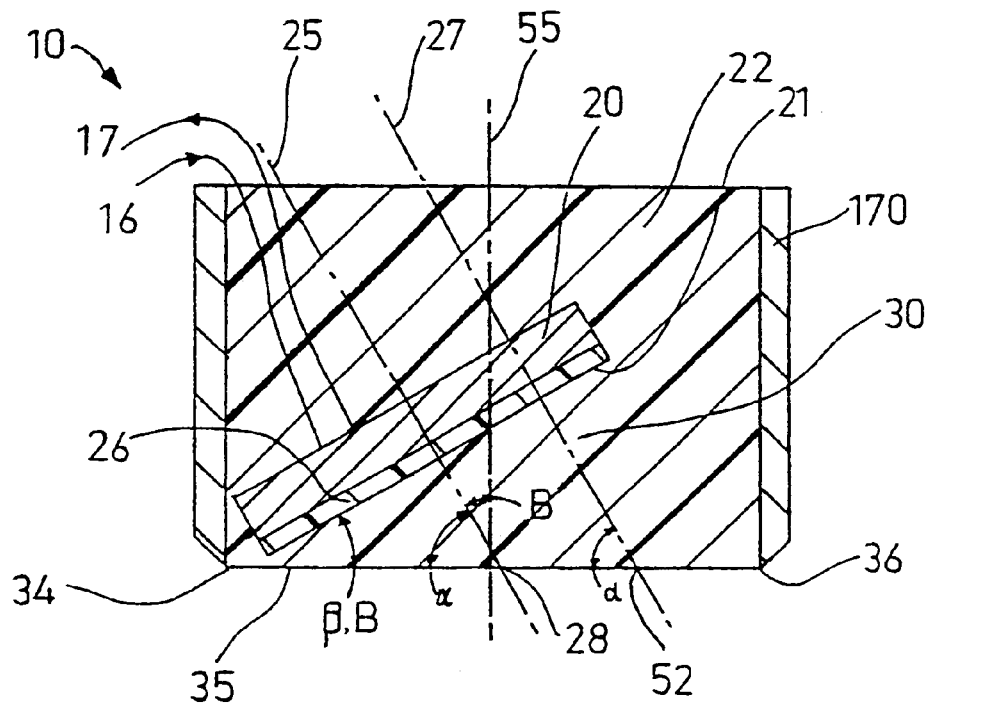
FIG. 1(a) is cross sectional view of the embodiment shown in FIG. 1(b) taken along A—A.

The present invention relates to a probe for the detection of smooth surface lesions of a tooth crown surface, comprising an ultrasonic surface wave generator capable of transmitting surface ultrasonic waves along a tooth crown surface and an ultrasonic surface wave receiver capable of receiving ultrasonic surface wave reflections produced at smooth surface lesions that may be present on said tooth surface. Typically, said surface waves migrate along said tooth crown surface and are at least partially reflected at a said lesion if present. The functions of generating surface ultrasonic waves and of receiving such waves typically may be carried out by the same component. Thus, preferably, said ultrasonic surface wave generator and said ultrasonic surface wave receiver are unitary constituting an ultrasonic surface wave generator/receiver.

The relative positional terms "proximal" and "distal", respectively designated (P) and (D) in the Figures, herein refer to directions away from and towards the tooth crown surface, respectively, unless otherwise specified.

The present invention also relates to a probe for the detection of smooth surface lesions of a tooth crown surface, wherein said ultrasonic surface wave generator comprises a suitable first ultrasonic transducer, capable of transmitting ultrasonic waves via a distal face thereof, and wherein said ultrasonic surface wave receiver comprises a suitable ultrasonic transducer capable of receiving ultrasonic wave reflections via a distal face thereof, wherein said first transducer and said second transducer further comprise a coupler operatively connected to said transducers, said coupler having a contact surface, wherein at least one longitudinal axis through each said distal face and substantially perpendicular thereto intersects said contact surface distally with respect to the corresponding said distal face, and wherein said contact surface forms an angle β with said distal face substantially different from 0° at least at said intersection of each of said at least one longitudinal axis with said contact surface.

The present invention also relates to a probe for the detection of smooth surface lesions of a tooth crown surface, comprising an ultrasonic surface wave generator/receiver capable of transmitting surface ultrasonic waves along a tooth crown surface and capable of receiving ultrasonic surface wave reflections produced at smooth surface lesions that may be present on said tooth surface.

In particular, the present invention relates to a probe for the detection of smooth surface lesions of a tooth crown surface, wherein said ultrasonic surface wave generator/receiver comprises a single ultrasonic transducer, capable of transmitting ultrasonic waves and receiving ultrasonic wave reflections via a distal face thereof, and further comprises a coupler operatively connected to said transducer and having a contact surface, wherein at least one longitudinal axis through said distal face and substantially perpendicular thereto intersects said contact surface distally with respect to said distal face, and wherein said contact surface forms an angle β with said distal face substantially different from 0° at least at said intersection of said at least one longitudinal axis with said contact surface.

The present invention also relates to a probe for the detection of smooth surface lesions of a tooth crown surface, such as for example tooth crown surface cracks or primary or secondary caries, comprising an ultrasonic transducer, capable of transmitting ultrasonic waves and receiving ultrasonic wave reflections via a distal face thereof, and further comprising a coupler operatively connected to said transducer and having a contact surface, wherein at least one longitudinal axis through said distal face and substantially perpendicular thereto intersects said contact surface distally with respect to said distal face, and wherein said contact surface forms an angle β with said distal face substantially greater than 0° and smaller than 90° at least at said intersection of said at least one longitudinal axis with said contact surface. Thus, when said contact surface is in substantial contact with a tooth crown surface at least at said intersection of said at least one longitudinal axis with said contact surface, ultrasonic waves generated by said ultrasonic transducer are imparted by said coupler onto said tooth crown surface as surface ultrasonic waves which migrate along said tooth crown surface, said lesions being identifiable as surface ultrasonic wave reflections produced thereat.

In particular, the present invention relates to a probe for the detection of smooth surface lesions of a tooth crown surface, comprising an ultrasonic transducer, capable of transmitting ultrasonic waves and receiving ultrasonic wave reflections via a distal face thereof, and further comprising a coupler operatively connected to said distal face of said transducer and having a contact surface distal to said transducer, wherein said transducer is a focused transducer comprising at least one focusing element capable of at least partially focusing ultrasonic sound waves generated by said transducer along a principal axis of the said focusing element at least within said coupler. The said coupler comprises a wedge angle B between a plane substantially perpendicular to the said principal axis of the said focusing element and a plane substantially tangential to the said contact surface at least at the intersection of said principal axis with said contact surface, said wedge angle B being substantially different from 0°, whereby, when said contact surface is in substantial contact with a tooth crown surface at least at said intersection of said principal axis with said contact surface, ultrasonic waves generated by said ultrasonic transducer are imparted by said coupler onto said tooth crown surface as surface ultrasonic waves which migrate along said tooth crown surface, said ultrasonic waves being at least partially focused along said principal axis at least within said coupler, and said lesions being detectable as surface ultrasonic wave reflections produced thereat received by said transducer.

Figure 1B:
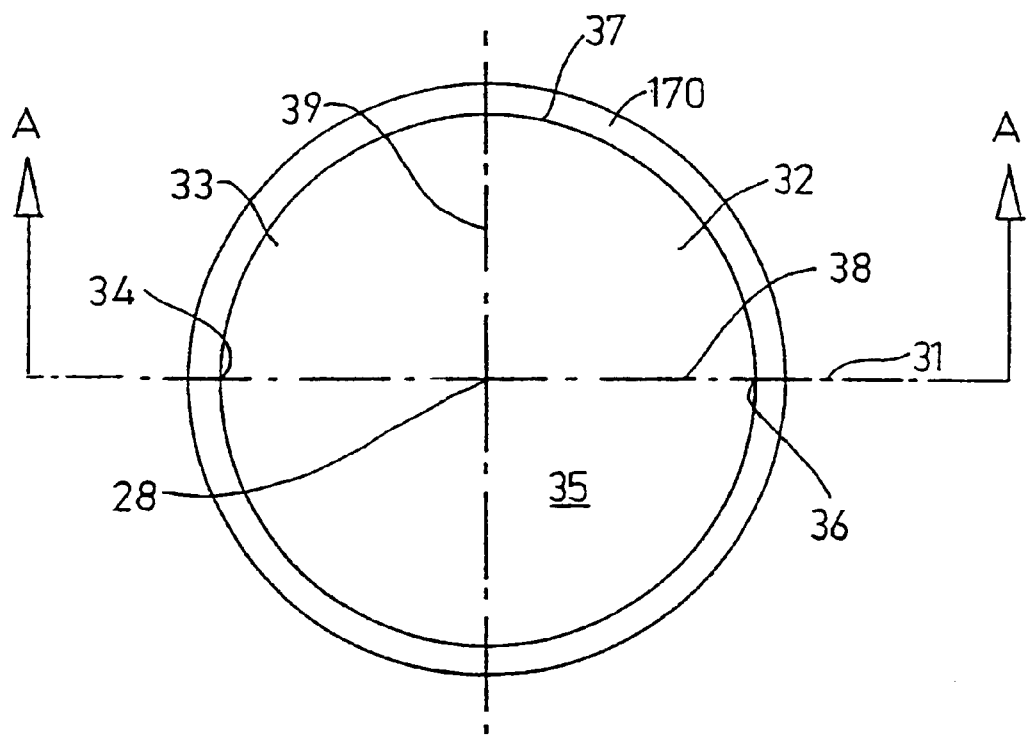
FIG. 1(b) is a bottom view of this embodiment.
Figure 2A:
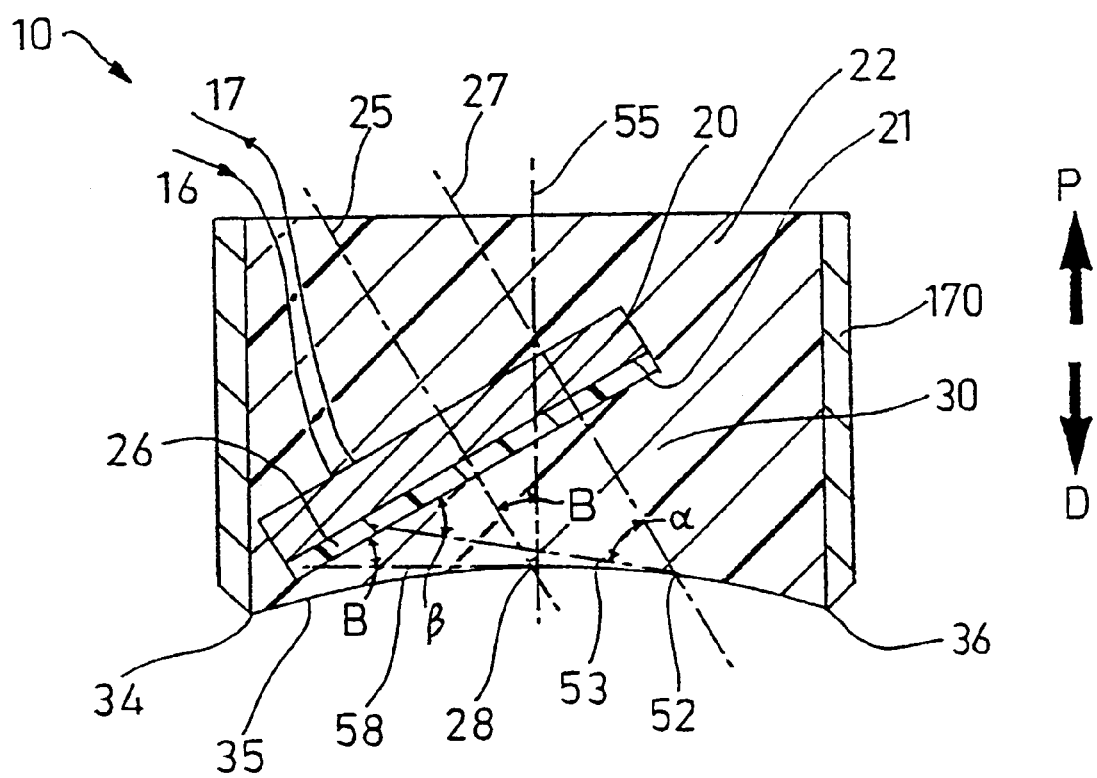
FIG. 2(a) is cross sectional view of the embodiment shown in FIG. 2(b) taken along B—B.
Figure 2B:
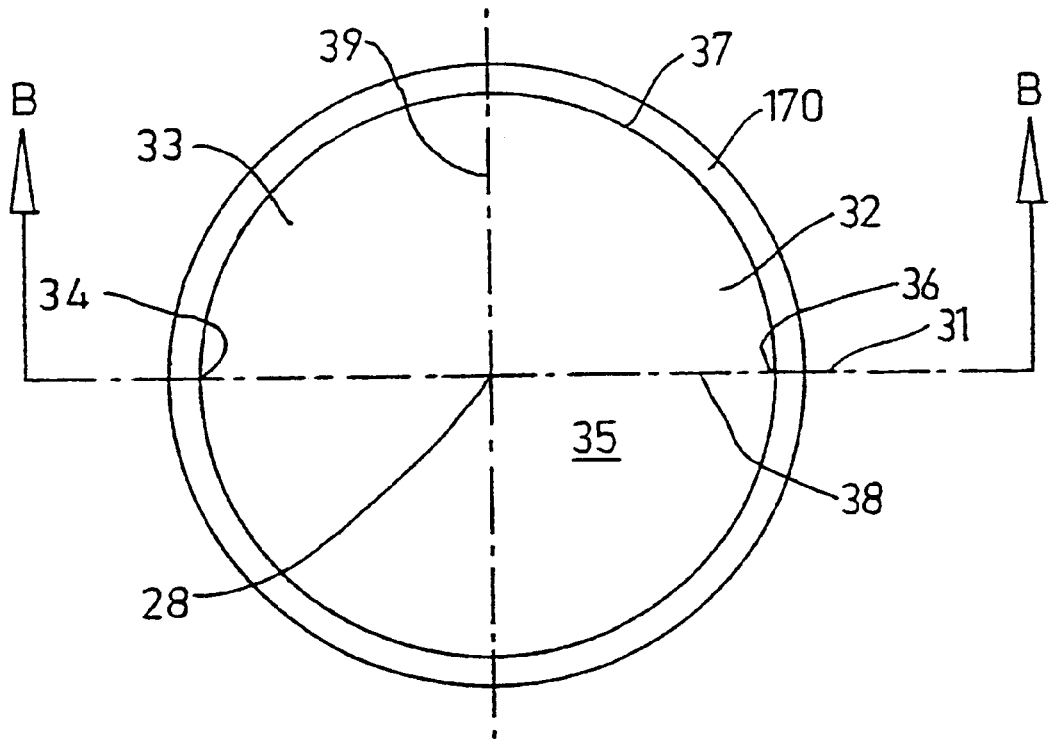
FIG. 2(b) is a bottom view of this embodiment.
Figure 10A:
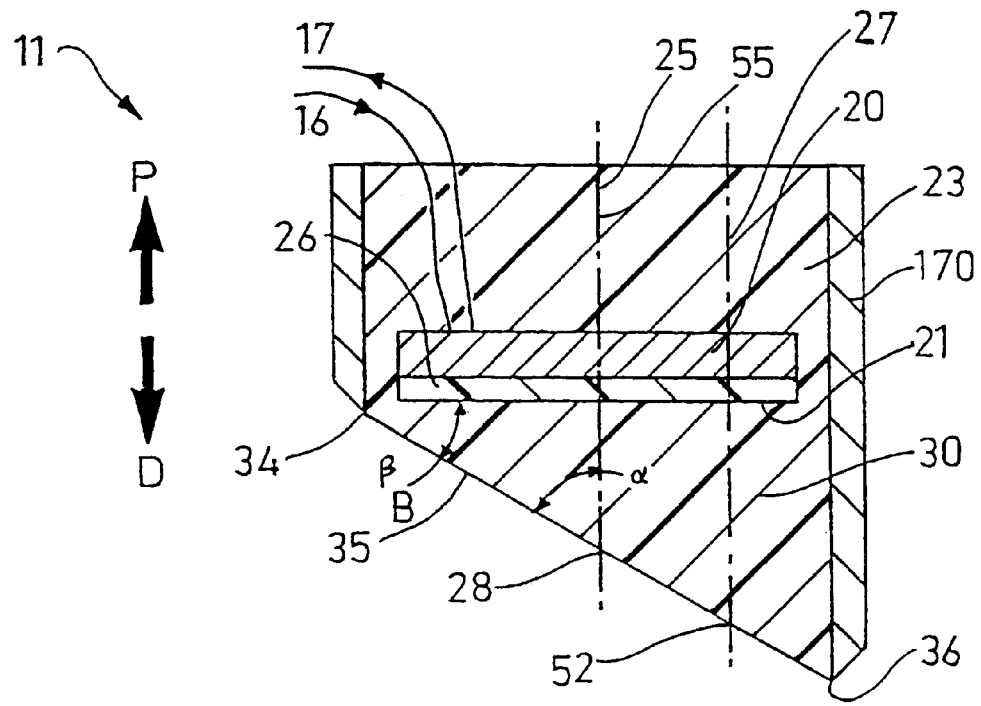
FIG. 10(a) is cross sectional view of the embodiment shown in FIG. 10(b) taken along C—C.
Figure 10B:
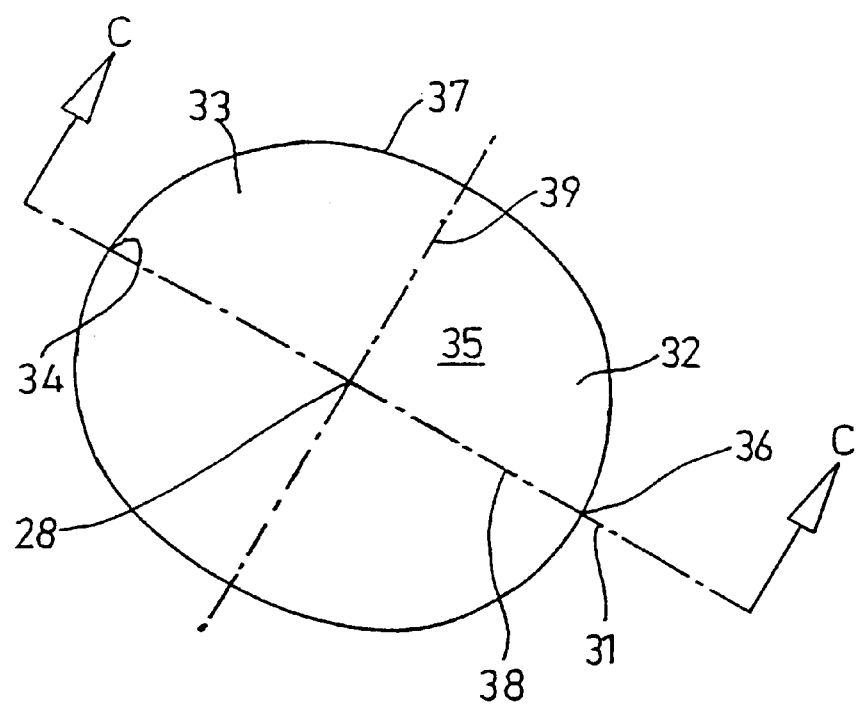
FIG. 10(b) is a bottom view of this embodiment.

FIGS. 1 and 2 depict the overall concept of the probe according to the first and second embodiments of the present invention. FIGS. 3, 4, 5, 6, 7, and 8 depict the overall concept of the probe according to a third, fourth, fifth, sixth, seventh and eighth embodiment of the present invention comprising spot-focused transducers. FIG. 9 depicts the overall concept of the present invention according to a ninth embodiment of the present invention comprising a line-focused transducer. FIG. 10 depicts the overall concept of the probe according to a tenth embodiment of the present invention.

The said probe, designated (10), comprises an ultrasonic transducer (20), comprising a piezoelectric crystal (26) having a transducer distal face (21), and a coupler (30), typically wedge-like, said coupler (30) having a contact surface (35), for contacting or abutting against a tested tooth crown surface, wherein said contact surface (35) is operatively connected to said transducer (20). Said crystal (26) is typically a simple or composite piezoelectric crystal.

The central longitudinal axis (25) of the transducer (20) is herein defined as an imaginary line passing longitudinally through substantially the center of the transducer (20) and substantially the centre of the said transducer distal face (21). A longitudinal axis (27) of the transducer (20) is herein defined as an imaginary line passing through the transducer distal face (21) of the said transducer (20) and parallel to said central longitudinal axis (25).

In the first, second and tenth embodiments of the present invention, the said probe (10) comprises an unfocused transducer (20), wherein the transducer distal face (21) thereof, i.e. of the crystal (26), is substantially planar, as illustrated in FIGS. 1, 2 and 10. Ultrasonic sound waves generated by the transducers in these embodiments are essentially unfocused save for natural diffraction effects in the near field.

In the third, fourth, fifth, sixth, seventh, eighth and ninth embodiments, the said transducer (20) is a focused transducer.

Focused transducers are herein defined as ultrasonic transducers capable of substantially focusing ultrasonic sound waves to an extent substantially greater than is normally achieved from natural diffraction effects with an isolated but similar non-focused transducer having a planar transducer distal face, for example, in particular by means of at least one focusing element. The focusing element may be integral with the transducer, and consist, for example, of the distal face of the focused transducer, the distal face being substantially concave with a concavity having an overall curvature substantially sufficient to enable ultrasonic sound waves generated by the focused transducer to be at least partially focused. Alternatively, the focusing element may be separate from the transducer, comprising focusing means such as suitable lenses, mirrors and phase plates. There are two general categories of focusing transducers: (I) spot-focused or spherically focused transducers; and (II) line-focused or cylindrical focus transducers.

In particular, the focused transducers comprised in the third, fourth, fifth, sixth, seventh and eighth embodiments of the present invention are spot-focused transducers, while the focused transducer comprised in the ninth embodiment of the present invention is a line-focused transducer.

In the spot-focused transducer of the said third, fourth, fifth, sixth, seventh and eighth embodiments of the present invention, ultrasonic sound waves are partially or fully focused by means of the said focusing element in a direction substantially along a principal axis, herein defined as the direction of maximum response of the spot-focused transducer, and particularly towards the focus of the focusing element, which may be a point or a region on the said principal axis, depending on the focusing properties of the focusing element.

Structurally, the principal axis of a spot-focused transducer typically intersects the focusing element of the transducer distally at substantially the center thereof. Where said focusing element comprises an axisymmetrical converging or diverging surface, the principal axis of the focusing element, and therefore of the transducer, is typically substantially co-aligned with the axis of rotation (or of symmetry) of the converging or diverging surface, respectively, of the focusing element. Where the said focusing element comprises a non-axisymmetric surface, the principal axis of the focusing element (and therefore of the transducer) may be similarly defined in suitable geometrical terms consistent with the direction of maximum response of the transducer via said focusing element.

In the line-focused transducer of the said ninth embodiment of the present invention, ultrasonic sound waves are partially or fully focused by means of the said focusing element in a direction substantially along a principal band (rather than just a principal axis), herein defined as the direction and width of maximum response of the line-focused transducer.

Structurally, the principal band of a line-focused transducer typically intersects the focusing element of the transducer distally along substantially one spatial axis thereof. In general, the focusing element of line-focused transducers is two-dimensional in character, rather than axisymmetric, having focusing characteristics substantially along only two out of the three spatial axes, say the first (x-) and second (y-) axes. The said principal band is substantially orthogonal in direction to the third (z-) axis. The profile of the focusing element for line-focused transducers along planes parallel to the first (x-) and second (y-) axes is generally substantially constant along the said third (z-) axis. The principal band may thus be regarded as the locus of local principal axes obtained from each such profile along the said third (z-) axis. The overall principal axis of a line-focused transducer is herein defined as an imaginary line substantially parallel to, within and substantially at the centre of the said principal band of the line-focused transducer.

In embodiments comprising a spot-focused transducer or an unfocused transducer, the transducer typically comprises a substantially circular distal face (21), while in embodiments comprising a line-focused transducer, the transducer typically comprises a rectangular distal face (21).

Figure 3A:
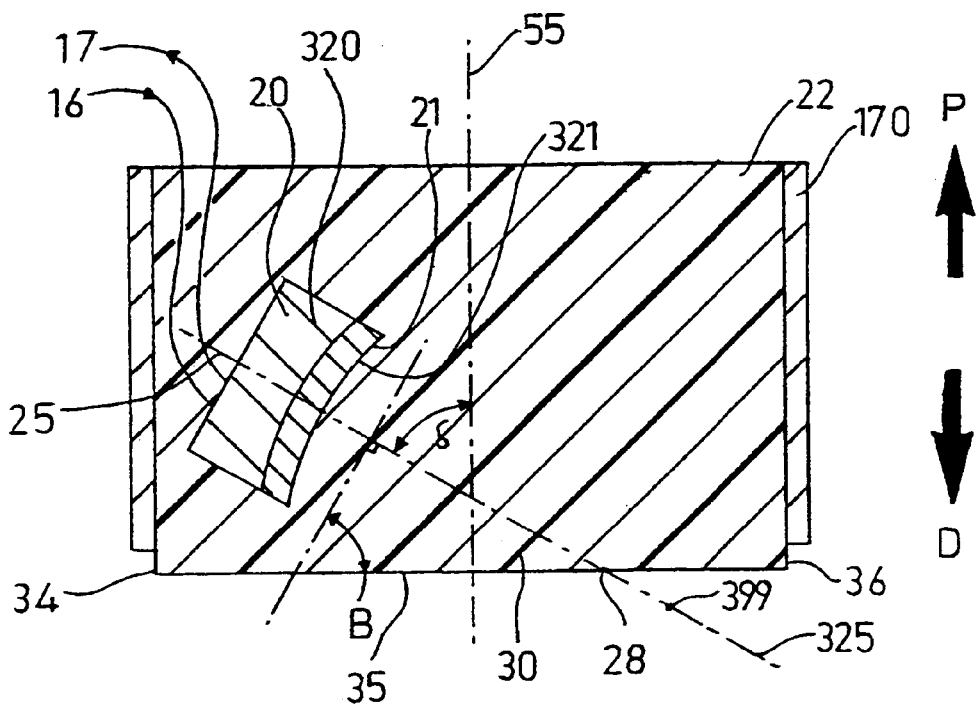
FIG. 3(a) is cross sectional view of the embodiment shown in FIG. 3(b) taken along D—D.
Figure 3B:
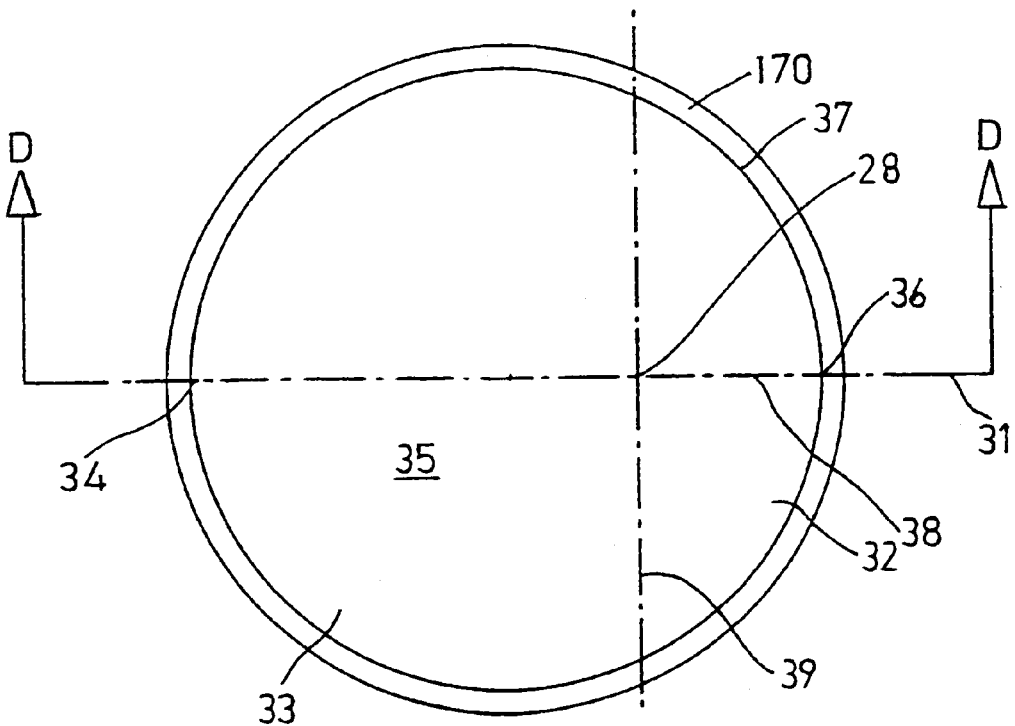
FIG. 3(b) is a bottom view of this embodiment.

Thus, in the third embodiment of the present invention, the said transducer (20) is a spot-focused transducer (320), wherein the said focusing element consists of said transducer distal face (21) of the transducer (320), said distal face (21) being substantially concave with a concavity (321), as illustrated in FIG. 3. In this embodiment, the concavity (321) is substantially axisymmetric about the principal axis (325) thereof. Further, in this embodiment, the principal axis (325) of the concavity (321) is substantially co-aligned with the central longitudinal axis (25) of the transducer (320). The concavity (321) has an overall curvature substantially sufficient as to enable ultrasonic waves generated by said transducer (320) to be at least partially focused at least within said wedge coupler (30). The curvature of said concavity (321) may be optionally substantially spherical. Alternatively, said concavity (321) may have a curvature substantially parabolic in longitudinal cross-sectional profile, or any other curvature capable of substantially focusing said ultrasonic waves generated by said focused transducer (320) towards said principal axis (325), at least within the said coupler (30). The focus (399) of the transducer is located substantially on said principal axis (325), preferably distally from said contact surface (35).

Figure 4A:
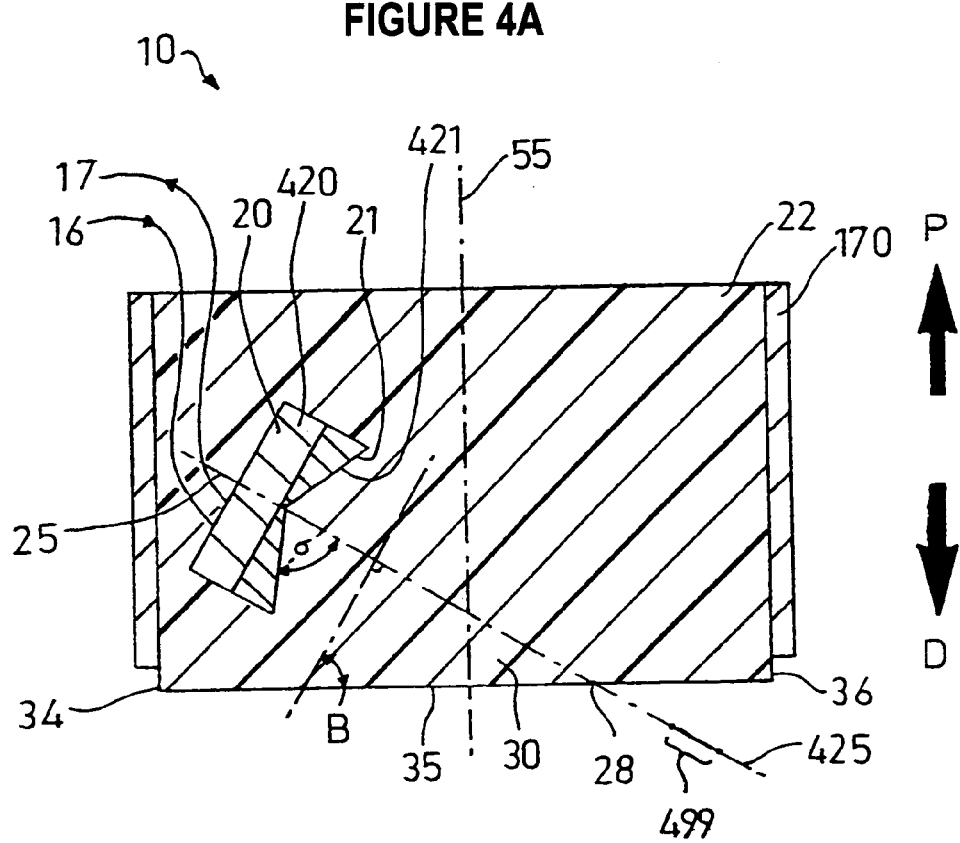
FIG. 4(a) is cross sectional view of the embodiment shown in FIG. 4(b) taken along E—E.
Figure 4B:
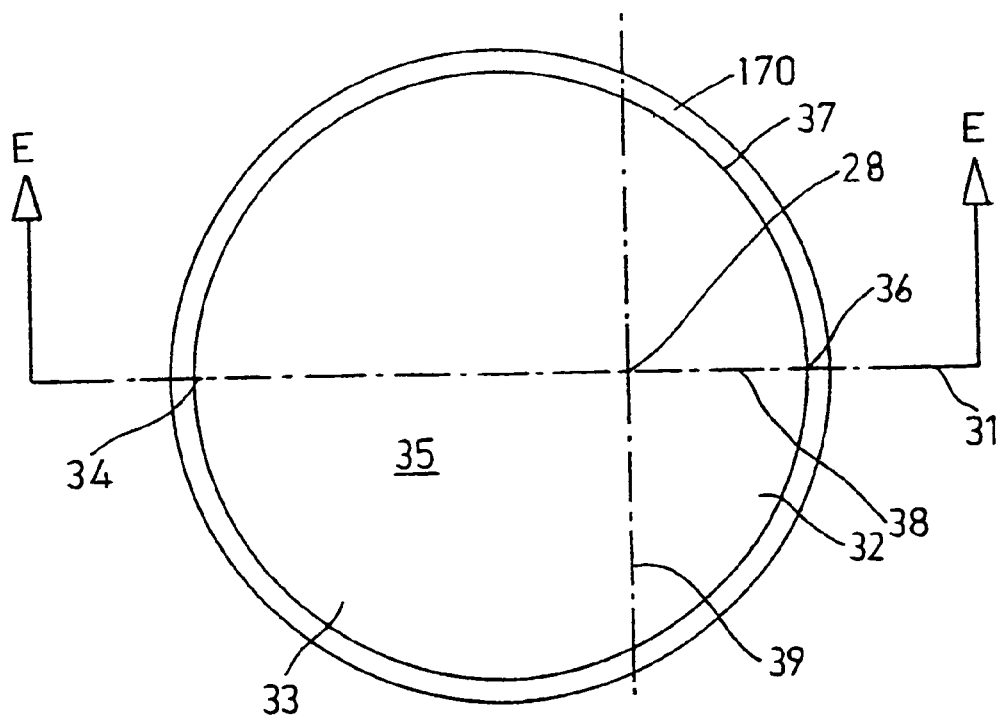
FIG. 4(b) is a bottom view of this embodiment.

In the fourth embodiment of the present invention, the said transducer (20) is a spot-focused transducer (420), wherein the said focusing element consists of said transducer distal face (21) of the transducer (420), said distal face (21) being substantially concave with a cone-shaped concavity (421), as illustrated in FIG. 4. In this embodiment, the cone-shaped concavity (421) is substantially axisymmetric about the principal axis (425). Further, in this embodiment, the said concave surface principal axis (425) is substantially co-aligned with the central longitudinal axis (25) of the transducer (420). While such a cone-shaped concavity (421) does not have a focal point per se, the cone-angle σ may be nevertheless be chosen such as to enable ultrasonic waves generated by said transducer (420) to be at least partially focused in a direction towards the said principal axis (425), at least within the said coupler (30). The said cone-angle σ is as the angle between the cone-shaped concavity (421) and the said principal axis (425) taken on any plane that intersects the said the cone-shaped concavity (421) and the said principal axis (425). The said cone-shaped cone-shaped concavity (421) comprises a focal region (499) towards which maximum focusing of ultrasonic waves generated by said transducer (420) is generally directed. Said focal region (499) is substantially aligned with said principal axis (425) and is preferably located distally from said contact surface (35).

Figure 5A:
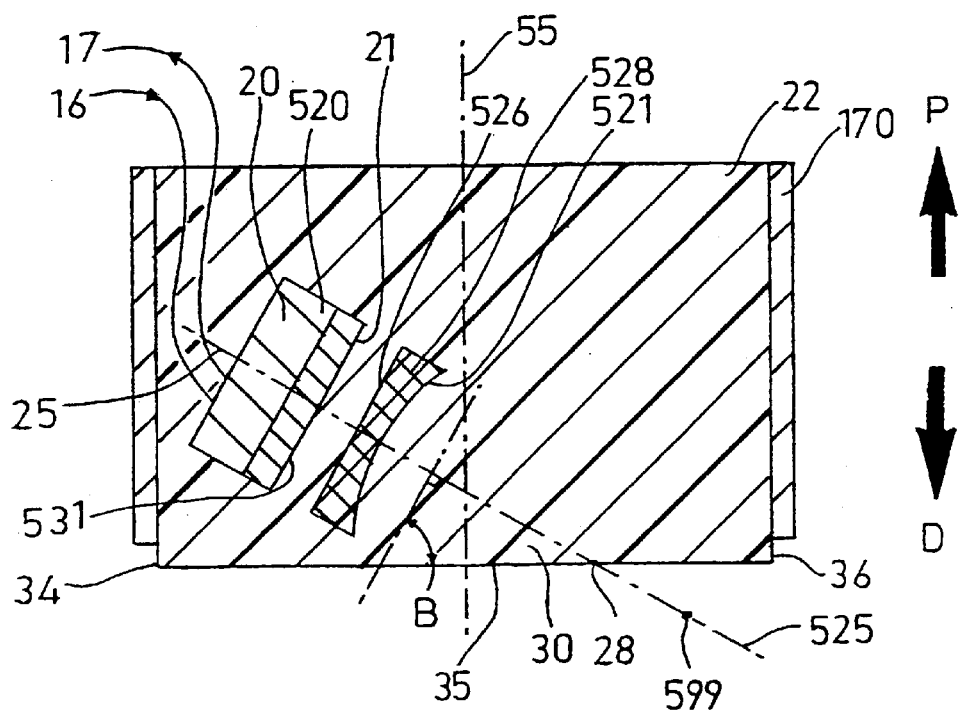
FIG. 5(a) is cross sectional view of the embodiment shown in FIG. 5(b) taken along F—F.
Figure 5B:
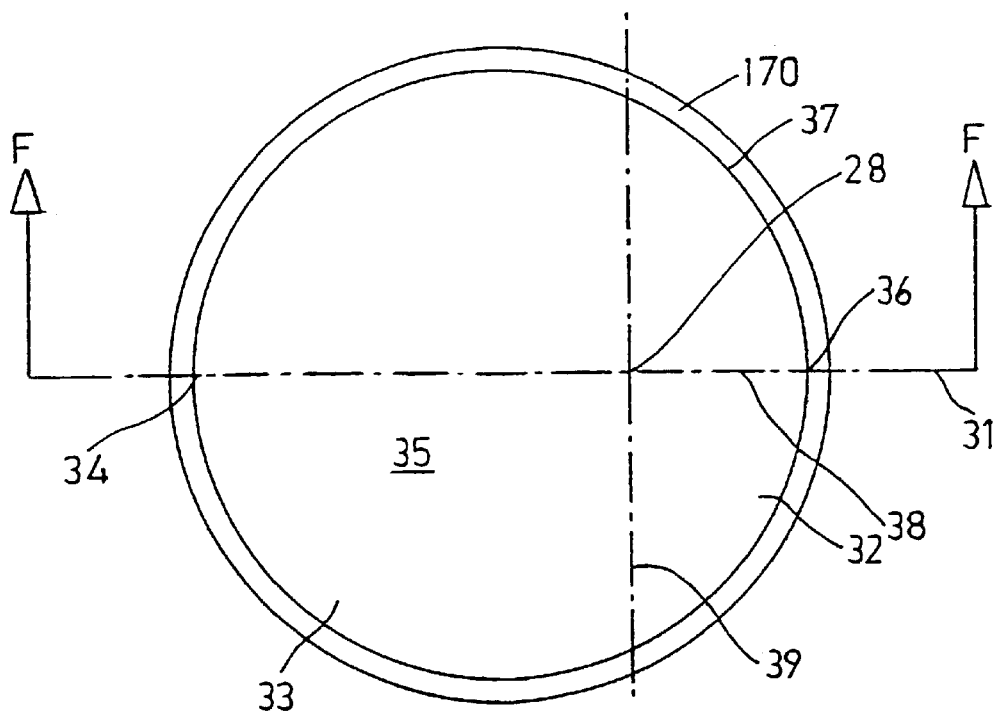
FIG. 5(b) is a bottom view of this embodiment.

In the fifth embodiment of the present invention, the said transducer (20) is a spot-focused transducer (520), having a transducer distal face (21) which comprises a substantially planar surface (531). The said focusing element in this embodiment comprises a suitable plane-concave lens (528) intermediate said transducer distal face (21) of transducer (520) and said contact surface (35) of the coupler (30), as illustrated in FIG. 5. In this embodiment, said plane-concave lens (528) comprises a substantially planar proximal face (526) and a substantially concave distal face (521). The said concave distal face (521) is substantially axisymmetric about the principal axis (525) of the plane concave lens (528), said principal axis (525) typically passing through substantially the center of the distal face (521). In the present embodiment, the said principal axis (525) of the plane-concave lens (528) is substantially aligned with the central longitudinal axis (25) of the transducer (520), and thus the principal axis of the spot focused transducer (520) as a whole including the said lens (528) is thus substantially co-aligned with the said principal axis (525) of the plane-concave lens (528). The concave distal face (521) has a concavity sufficient as to enable ultrasonic waves generated by said transducer (520) to be at least partially focused along said principal axis (525), at least within said wedge coupler (30). The said concave face (521) may comprise a surface which may be optionally substantially spherical or parabolic in curvature, or any other curvature capable of substantially focusing said ultrasonic sound waves generated by said focused transducer (520) towards said principal axis (525), at least within the said coupler (30). The focus (599) (or equivalent focal region, where appropriate) of the transducer (520) is located substantially on said principal axis (525), preferably distally from said contact surface (35).

Figure 6A:
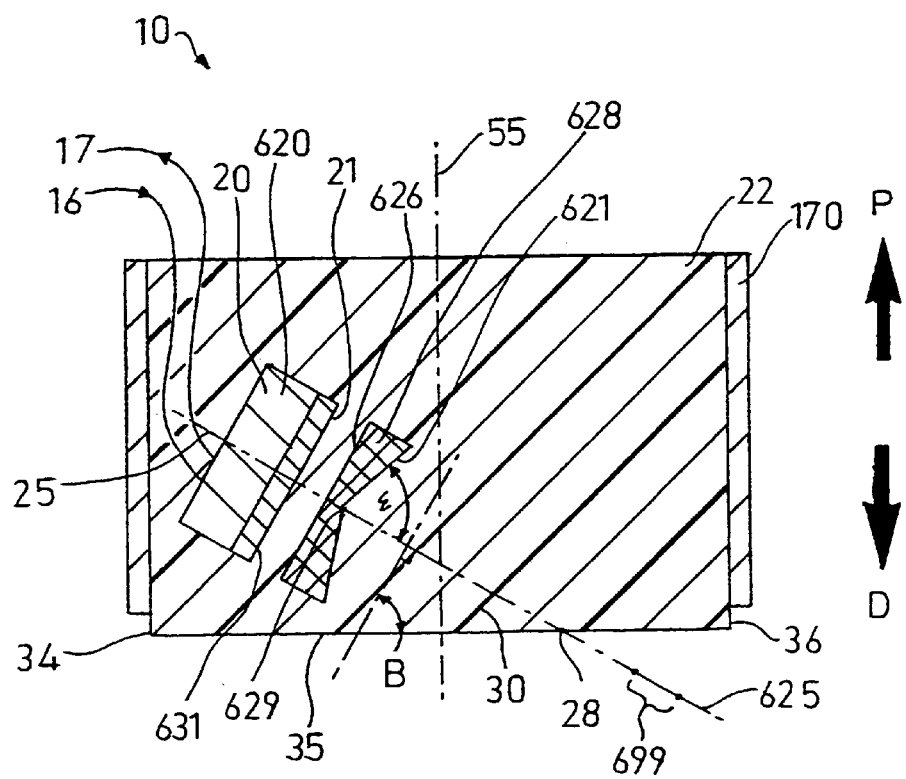
FIG. 6(a) is cross sectional view of the embodiment shown in FIG. 6(b) taken along G—G.
Figure 6B:
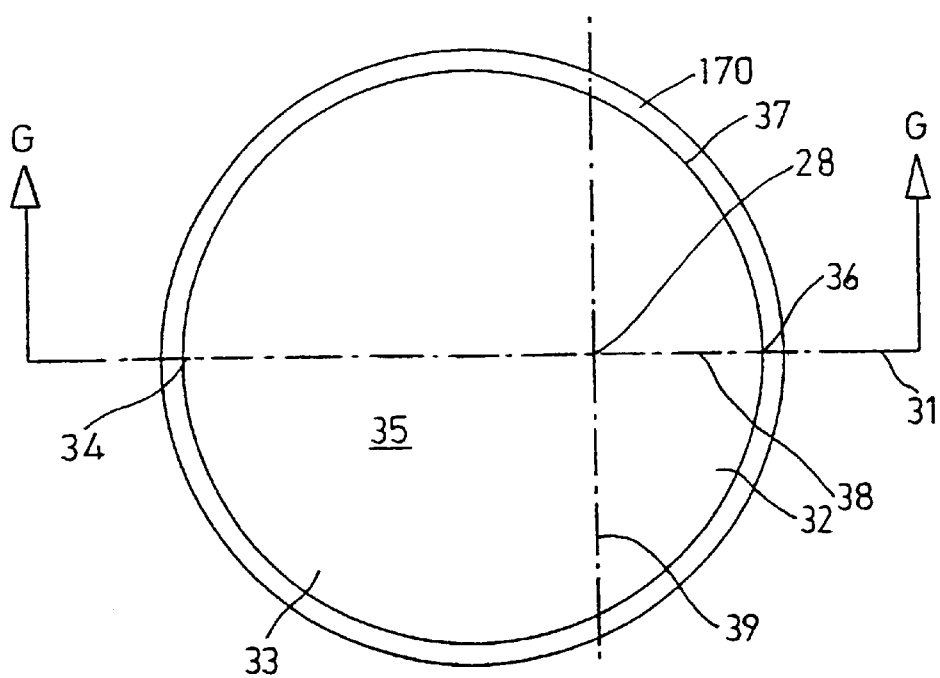
FIG. 6(b) is a bottom view of this embodiment.

In the sixth embodiment of the present invention, the said transducer (20) is a spot-focused transducer (620), having a transducer distal face (21) which comprises a substantially planar surface (631). The said focusing element in this embodiment comprises a suitable cone-shaped converging lens (628) intermediate said transducer distal face (21) of said transducer (620) and said contact surface (35) of the coupler (30), as illustrated in FIG. 6. In this embodiment, said cone-shaped converging lens (628) comprises a substantially planar proximal face (626) and a substantially concave cone-shaped distal face (621). The said cone-shaped distal face (621) is substantially axisymmetric about the principal axis (625) of the cone-shaped converging lens (628), said principal axis (625) typically passing through the apex (629) of the distal face. In this embodiment, the said principal axis (625) of the cone-shaped distal face (621), and therefore of the transducer (620), is substantially aligned with the central longitudinal axis (25) of the transducer (620). While such a cone-shaped converging lens (628) does not have a focal point per se, the cone-angle ε may nevertheless be chosen such as to enable ultrasonic waves generated by said transducer (620) to be at least partially focused in a direction towards the said principal axis (625) of the cone-shaped distal face (621), at least within the said coupler (30). The said cone-angle ε is as the angle between the concave face (621) and the said principal axis (625) taken on any plane that intersects the said the concave face (621) and the said principal axis (625). The said cone-shaped concave face (621) comprises a focal region (699) towards which maximum focusing of ultrasonic waves generated by said transducer (620) is generally directed. Said focal range (699) is substantially aligned with said principal axis (625) and is preferably located distally from said contact surface (35).

Figure 7A:
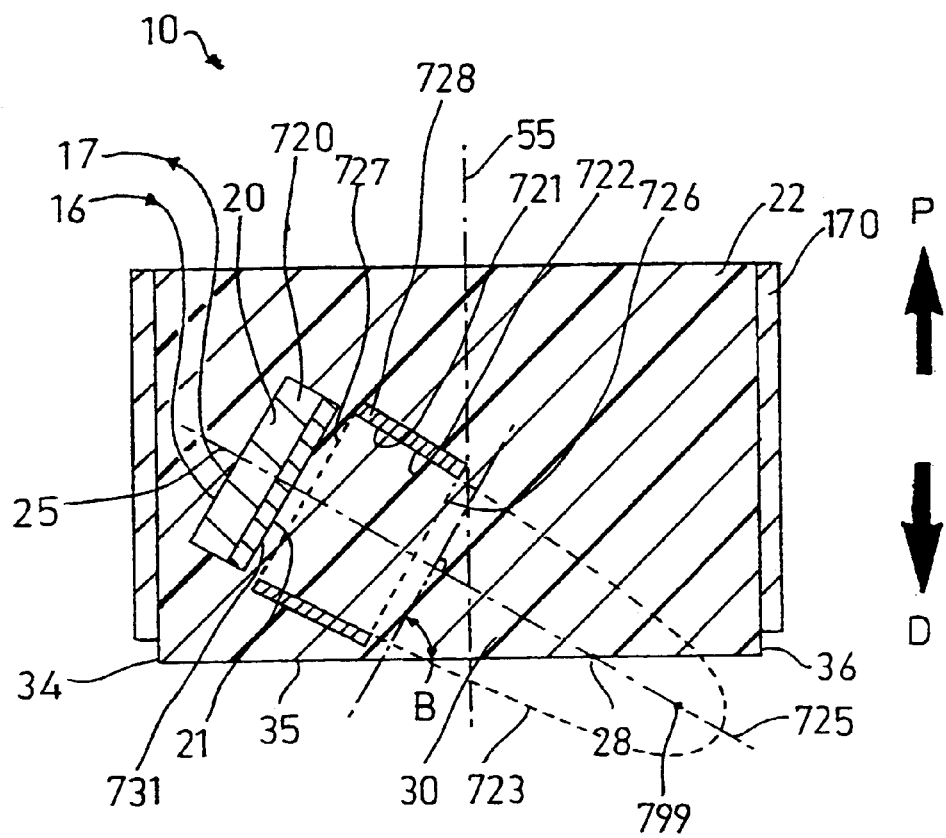
FIG. 7(a) is cross sectional view of the embodiment shown in FIG. 7(b) taken along H—H.
Figure 7B:
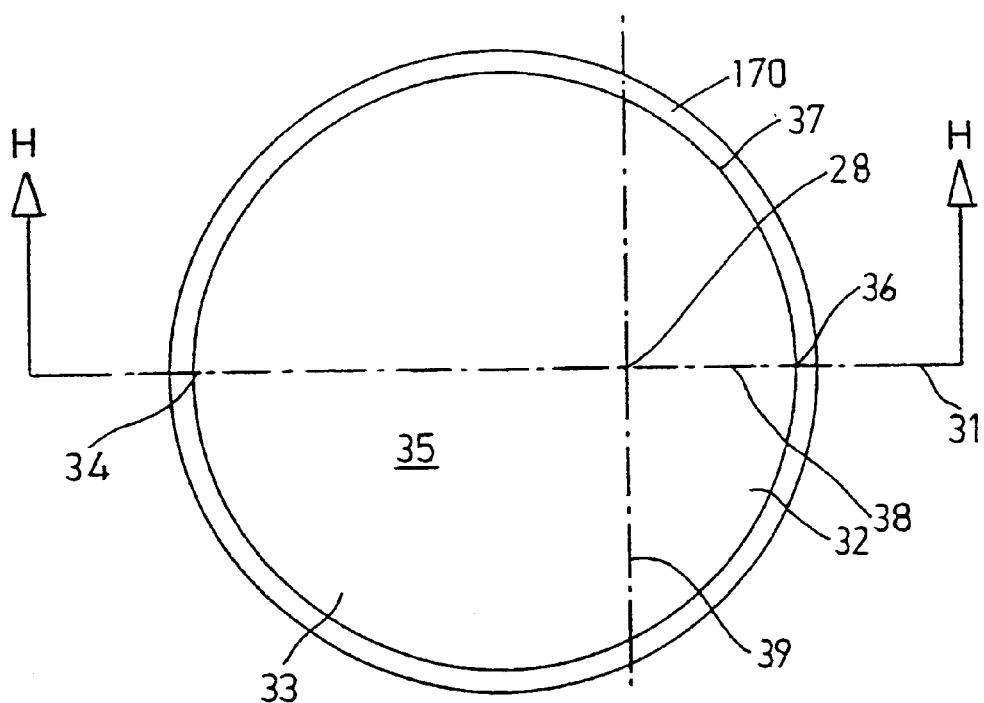
FIG. 7(b) is a bottom view of this embodiment.

In the seventh embodiment of the present invention, the said transducer (20) is a spot-focused transducer (720), having a said transducer distal face (21) which comprises a substantially planar surface (731). In this embodiment, the said focusing means comprises a hollow reflecting mirror (728) intermediate said transducer distal face (21) and said contact surface (35), as illustrated in FIG. 7. Said reflecting mirror (728) is characterised in comprising a distal opening (726) proximal and near to said contact surface (35), a proximal opening (727) distal and near to said transducer distal face (21) of said transducer (720), and an inner reflecting converging surface (721). The said inner reflecting converging surface (721) preferably comprises a suitably converging profile (722) sufficient as to enable ultrasonic waves generated by said transducer to be at least partially focused along the principal axis (725) of the hollow mirror (728) at least within said wedge coupler (30). For example, said profile (722) may be parabolic about the said principal axis (725) as illustrated by the dotted line (723) in FIG. 7(a). The converging surface (721) may then be defined, for example, as the surface of the body of revolution of the profile (722) about the said principal axis (725), in which the apex of the body of revolution preferably comprising the focus (799) of the parabola is truncated. In this embodiment, the said converging surface (721) is thus substantially axisymmetric about said principal axis (725), which preferably passes through substantially the centers of the said distal opening (726) and the said proximal opening (727). In this embodiment, the said principal axis (725) of the said mirror (728), is substantially aligned with the central longitudinal axis (25) of the transducer (720). The focus (799) (or equivalent focal region, where appropriate) of the transducer (720) is located substantially on said principal axis (725), preferably distally from said contact surface (35). The converging mirror surface (721) thus has a profile such as to enable ultrasonic waves generated by said transducer (720) to be at least partially focused along said principal axis (725) at least within said wedge coupler (30).

Figure 8A:
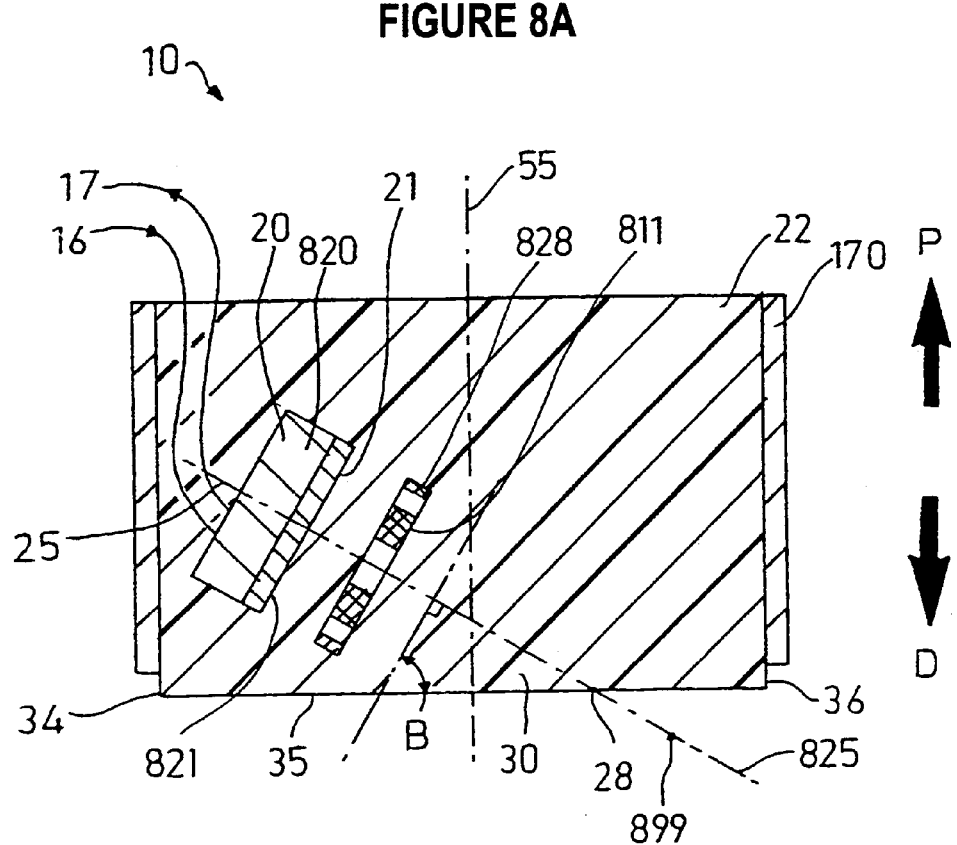
FIG. 8(a) is cross sectional view of the embodiment shown in FIG. 8(b) taken along I—I.
Figure 8B:
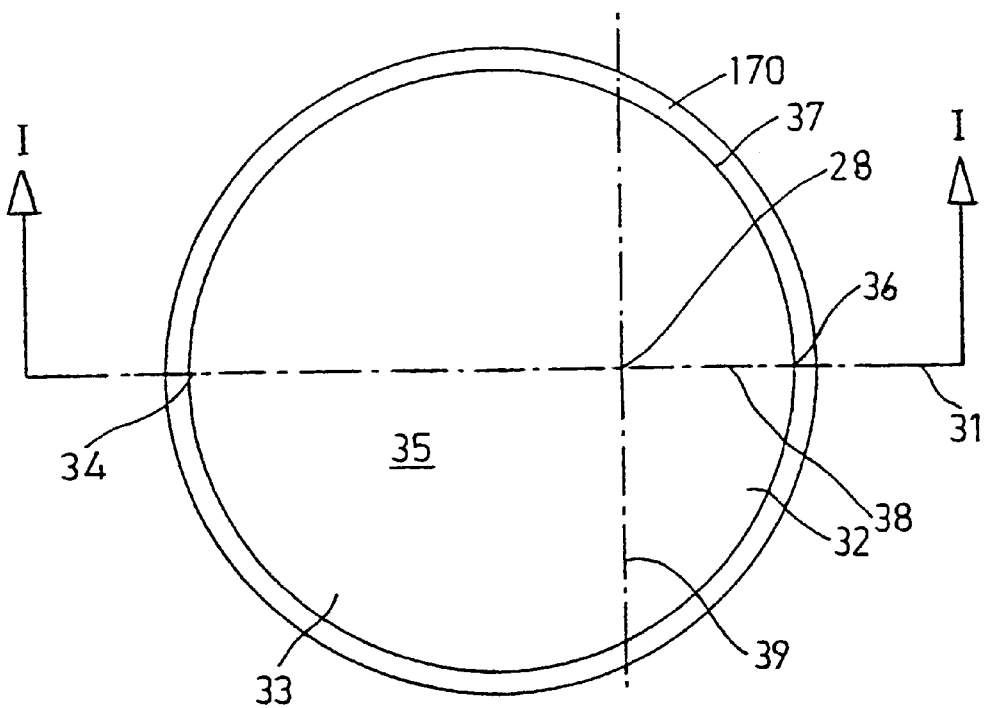
FIG. 8(b) is a bottom view of this embodiment.

In the eighth embodiment of the present invention, the said transducer (20) is a spot-focused transducer (820), having a said transducer distal face (21) which comprises a substantially planar surface (821). In this embodiment, the said focusing means comprises a suitable phase plate (828) intermediate said transducer distal face (21) of the said transducer (820) and said contact surface (35) of the coupler (30), as illustrated in FIG. 8. In this embodiment, the said phase plate (828) is substantially axisymmetric about the principal axis (825) thereof, said principal axis (825) preferably passing through substantially the center of the distal face (811) of the said phase plate (828). The said principal axis (825) of said phase plate (828) is substantially aligned with the central longitudinal axis (25) of the transducer (820) in this embodiment. The focus (899) of the transducer (820) is located substantially on said principal axis (825), preferably distally from said contact surface (35). The said phase plate (828) is suitably configured such as to enable ultrasonic waves generated by said transducer (820) to be at least partially focused along said principal axis (825) at least within said wedge coupler (30).

In the ninth embodiment of the present invention, the said transducer (20) is a line-focused transducer (920), wherein said at least one focusing element consists of said distal face (21) of said focused transducer (920), said distal face being substantially cylindrically concave with a concavity (921), as illustrated in FIG. 9. The profile (922) of said concavity (921) is typically substantially constant along a third (z-) axis of the transducer (920), said third (z-) axis being substantially orthogonal to the central longitudinal axis (25) of the transducer (920) and to the minor axis (39) (hereinafter defined) of the contact surface (35). In this embodiment, the principal band (929), and in particular the principal axis (925), are aligned with the central longitudinal axis (25) of the transducer (920). The cylindrical concavity (921) has an overall curvature, i.e. profile (922), at least substantially sufficient to enable ultrasonic waves generated by said transducer (920) to be at least partially focused within said wedge coupler (30). The said profile (922) of said cylindrical concavity (921) may be optionally circular or parabolic in curvature, or any other curvature capable of substantially focusing said ultrasonic waves generated by said transducer (920) towards said principal band (929), at least within the coupler (30). The transducer (920) comprises a focal line (999) (or equivalent focal region, where appropriate), which may be defined as the locus of focal points of each said profile (922) along said third (z-) axis, preferably distally from said contact surface (35).

In the focused transducers of the third to ninth embodiments, the principal axis of the focusing element in each case is substantially co-aligned with the central longitudinal axis of the corresponding focused transducer. In other embodiments, it is possible to set the principal axis of the focusing element at an angle to the corresponding transducer central longitudinal axis.

Typically, all components of said probe (10) which may be brought into contact with or in very close proximity to the patient's mouth or teeth are made from a medically compatible material which is also sterilisable and preferably autoclavable.

Said contact surface (35) is typically planar, as illustrated schematically in FIGS. 1, and 3 to 10, but may alternatively comprise other suitable profiles. For example, said contact surface (35) may be concave with a concavity having an overall curvature substantially complementary to the convex curvature of the tooth (90). Alternatively, the concavity may have a curvature substantially greater or alternatively substantially smaller than the convex curvature of the tooth (90), in order to accommodate a range of tooth sizes. For embodiments comprising a coupler (30) which is made from a flexible material, application of pressure by said coupler (30) against the tooth surface increases the effective area of contact between the contact surface (35) and the tooth surface. The said coupler (30) is preferably made from polyurethane or silicone or any other suitable material. Said coupler (30), and also said contact surface (35) may be rigid. Alternatively, said coupler (30) and said contact surface (35) may be elastically distortable to conform to the profile or curvature of the tooth (90).

In the first, third, fourth, fifth, sixth, seventh, eighth and ninth embodiments of the present invention, the contact surface (35) is substantially planar and is at an angle to the transducer distal face (21) and distal thereto. In the first and second embodiments, the overall wedge angle B is conveniently defined as the angle between the said planar contact surface (35) and a plane substantially perpendicular to central longitudinal axis of the transducer. In the third to ninth embodiments, the overall wedge angle B may be defined as the angle between the said planar contact surface (35) and a plane substantially perpendicular to the principal axis of each corresponding embodiment. The said angle B is substantially greater than 0° and less than 90°.

Alternatively, contact surface (35) may be substantially non-planar—for example, substantially concave—in which case the following definitions may apply. Referring to the second embodiment (FIG. 2), for example, at least one said longitudinal axis (27) intersects said contact surface (35) at a point (52) distal from said transducer distal face (21): the contact surface (35) at said intersection point (52) forms an angle β with said transducer distal face (21). That is, the angle β between a plane parallel to the transducer distal face (21) and a plane substantially tangential to the contact surface (35) at intersection point (52) is considered the local wedge angle of the coupler (30) at point (52).

With focused transducers, as in for example the third to ninth embodiments, angle β may be similarly defined, mutatis mutandis, with the provision that point (52) is redefined as the intersection of an imaginary line parallel to the principal axis of each corresponding embodiment with the contact surface (35).

The overall wedge angle B of the coupler (30) may be defined in many different ways. In particular, the overall wedge angle B of said coupler (30) is geometrically related to said angle β obtained at the intersection (52) of said longitudinal axis (27), or alternatively of the principal axis, with said contact surface (35). For example, as shown in FIG. 2, the overall wedge angle B may be conveniently defined as the local wedge angle β between a plane perpendicular to the said central longitudinal axis (25) and a plane (58) substantially tangential to the contact surface (35) at the intersection point (28) of the central longitudinal axis (25) with the contact surface (30). In embodiments comprising focused transducers, point (28) is the intersection point between the principal axis of the focusing element of the corresponding focused transducer and the contact surface (35). Alternatively, the overall wedge angle B may be defined as the average of the local wedge angles β integrated over the whole or at least part of the contact surface (30). Alternatively, the overall wedge angle B of the coupler may be defined in other ways from the local wedge angle β. Alternatively, the wedge angle B may be defined as the angle between the said transducer distal face (21) and a plane defined by the perimeter (37) of the contact surface (35).

In particular for embodiments comprising focused transducers, the said overall wedge angle B is herein generally defined as the angle between a plane substantially perpendicular to the principal axis of the focusing element of the corresponding transducer and a plane substantially tangential to said contact surface (35) at the intersection of said principal axis with said contact surface (35), said wedge angle B being substantially different from 0°.

The major transverse plane (31) of the probe (10) is herein defined as a plane which is orthogonal to both, a plane parallel to the said transducer distal face (21) (in the case of non-focused transducers), and to a plane substantially tangential to the said contact surface (35) at said intersection point (28) of said central longitudinal axis (25) with said contact surface (35). For embodiments comprising focused transducers, the major transverse plane (31) of the probe (10) is herein defined as a plane which is orthogonal to both, a plane orthogonal to the principal axis of the focusing element of the corresponding focused transducer, and to a plane substantially tangential to the said contact surface (35) at said intersection point (28) of said central longitudinal axis (25) with said contact surface (35).

The optimum value for said overall wedge angle B of the coupler (30) may be determined from the equation:

$$B = \sin^{-1}(V_L/V_S) \pm E°$$

where $V_L$ is the longitudinal ultrasonic wave velocity in the coupler material, preferably in meters per second, and will thus vary with said material. $V_L$ may be determined for a particular coupler material in a manner known in the art. $V_S$ is the surface velocity of surface ultrasonic waves (in consistent units), which, for adult human dental enamel, has been determined empirically by the inventors to be of the order of 3143 meters per second, with maximum and minimum measured values of about 3416 and about 2957 meters per second, respectively. E° is a measure of the deviation from B in degrees wherein at least a major portion of the ultrasonic waves generated by the transducer (20) may be imparted as surface ultrasonic waves by said coupler (30) on a surface, when said contact surface is in substantial contact with said surface. Where contact surface (35) is non-planar, e.g. concave, E may also be regarded as a measure of the maximum acceptable deviation from angle B for the highest and lowest values of angle β obtained at the extremes of contact surface curvature. E° may be between 0° and 10°, or even higher than 10°, though preferably, it is between 2° to 3°.

The angle B is greater than 0° and less than 90°, preferably between about 10° and about 80°, and typically between 15° and 35°.

The value of $V_L$ for polyurethane is approximately 1500 meters per second, and thus, a coupler made from this material has an angle B of approximately 30°.

The value of $V_L$ for certain types of silicone may range from under about 900 meters per second to over about 1200 meters per second, depending on the specific type of silicone, and thus, a coupler made from this material may have an angle B correspondingly ranging from under about 17° to over about 22°.

Said transducer (20) is capable of generating and transmitting ultrasonic waves and also of receiving ultrasonic reflections, via said transducer distal face (21), in a manner known in the art.

Typically, ultrasonic waves of frequency in the range of about 2 MHz to about 20 MHz is provided by said transducer (20), through frequencies lower than 2 MHz or higher than 20 MHz may also be provided.

Said coupler (30) is preferably integral with a housing (22) which accommodates the probe (10, and the transducer distal face (21) of the said piezoelectric crystal (26) defines the operative transducer end of the said coupler (30). Nevertheless, the coupler (30) may be a separate component to the said housing (22). Preferably, and in particular when the said coupler (30) is made from a flexible material, said housing (22) comprises a substantially rigid outer wall or protective shell (170) around at least an external portion of the housing (22) including said coupler (30), with the exception of the said contact surface (35) which is left exposed. In the first and second embodiments, shown in FIGS. 1 and 2, respectively, the protective shell is tapered at the distal end thereof. Preferably, and as shown for the third to ninth embodiments in FIGS. 3 to 9, respectively, the shell (170) is truncated a small distance from the contact surface (35).

Said housing (22) has a central longitudinal axis (55), and in the first, second, third, fourth, fifth, sixth, seventh, eighth and ninth embodiments the said transducer distal face (21) of the transducer (20) is preferably inclined at an angle to the said housing longitudinal axis (55), such that the latter and the central longitudinal axis (25) of the transducer (20) are inclined to each other at an angle δ, substantially different from 0°. Said angle δ is preferably equal to the overall wedge angle B, as illustrated in FIGS. 1 to 9. However in embodiments comprising focused transducers, the said angle δ may be different to the wedge angle B, particularly when the principal axis of the focusing element is set at an angle to the central longitudinal axis (25) of the corresponding transducer.

Said contact surface (35) typically comprises a circular profile at its periphery, though in other embodiments, said contact surface may comprise other suitable profiles, for example, polygonal, oval, egg-shaped and superelliptical. A major axis (38) may be defined on said contact surface as the locus of intersection of said major transverse plane (31) with said contact surface (35). A minor axis (39) may then be defined on said contact surface (35) as a line thereon orthogonal to said major axis (38) and intersecting said intersection point (28). Said major axis (38) intersects the perimeter of the said contact surface at a leading edge (36) and trailing edge (34), wherein said leading edge (36) is more distally located with respect to said transducer distal face (21) than said trailing edge (34). Thus, said leading edge (36) is more distally located with respect to said transducer distal face (21) than said trailing edge (34). Said contact surface (35) may be divided at said minor axis (39) into a forward portion (32), comprising said leading edge (36), and a trailing portion (33) comprising said trailing edge (34).

In a tenth embodiment of the present invention, generally designated (11), as illustrated schematically in FIG. 10, angle δ is substantially equal to 0°, and thus the said housing longitudinal axis (55) is substantially parallel, and preferably coaxial with, the said central longitudinal axis (25) of the transducer (20). Thus, the said contact surface (35) is at angle β (at least at intersection point (28)) to said housing longitudinal axis (55) when viewed along said major transverse plane (31) as hereinbefore defined, as illustrated in FIG. 10.

In the tenth embodiment, said coupler (30) is typically of circular section at planes substantially perpendicular to said central longitudinal axis (25), so the perimeter (37) of the contact surface (35), when viewed substantially perpendicular to same, appears as an ellipse having a minor axis (39) and a major axis (38) along the said major transverse plane (31), which intersects the perimeter of the said contact surface (35) at leading edge (36) and trailing edge (34).

Alternatively, said coupler (30) may have a polygonal or other suitable cross-section at planes substantially perpendicular to said central longitudinal axis (25), wherein the contact surface (35) has a definable shape when viewed in a direction substantially perpendicular thereto, and wherein said definable shape may be attributed with a major axis and a minor axis, said major axis being located on said major transverse plane (31) and on said contact surface (35), and comprising a leading edge and trailing edge corresponding to said leading edge (36) and said trailing edge (34), respectively, as hereinbefore defined. Thus, said minor axis is similarly defined as being at right angles to said major axis and also as intersecting said central longitudinal axis (25).

Figure 11:
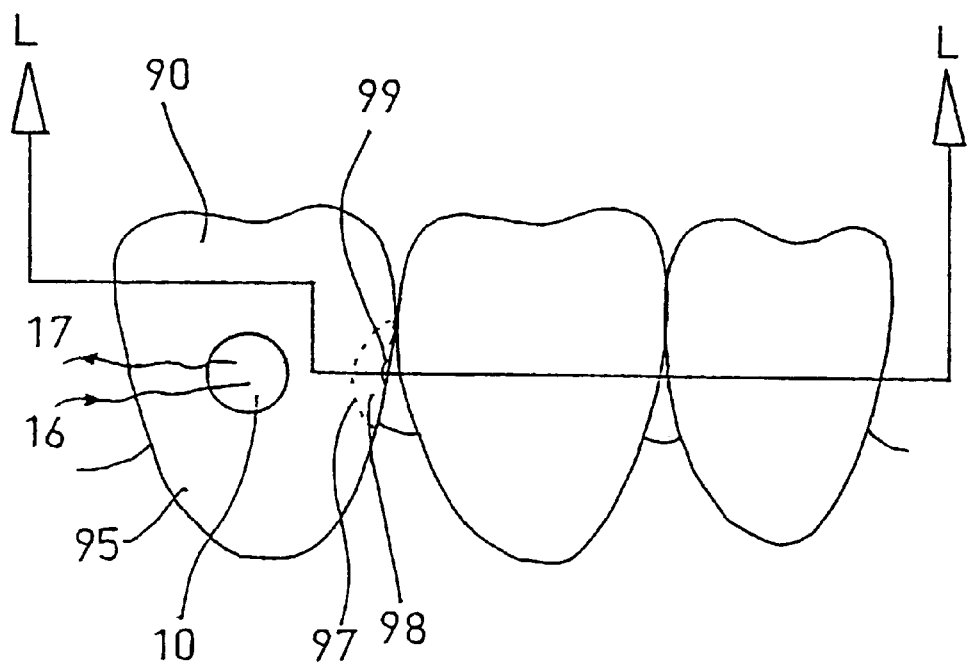
FIG. 11 shows in side view a portion of a dentition, with the probe of FIGS. 1 to 9 in contact with the crown surface of a tooth.
Figure 12:
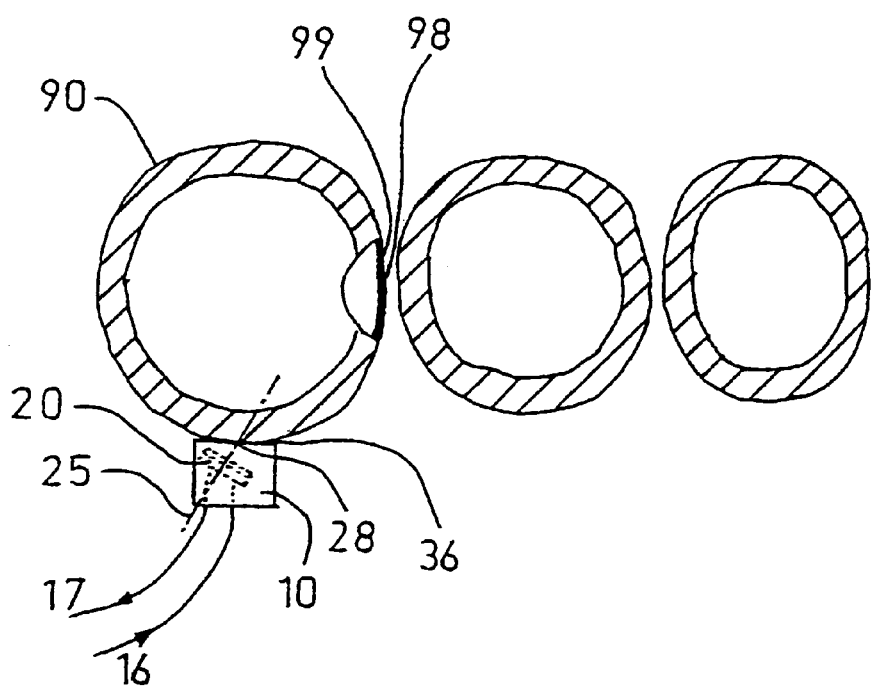
FIG. 12 is cross sectional view of the items shown in FIG. 11 taken along L—L, which represents a coronal section at the level of an interproximal caries lesion.
Figure 13:
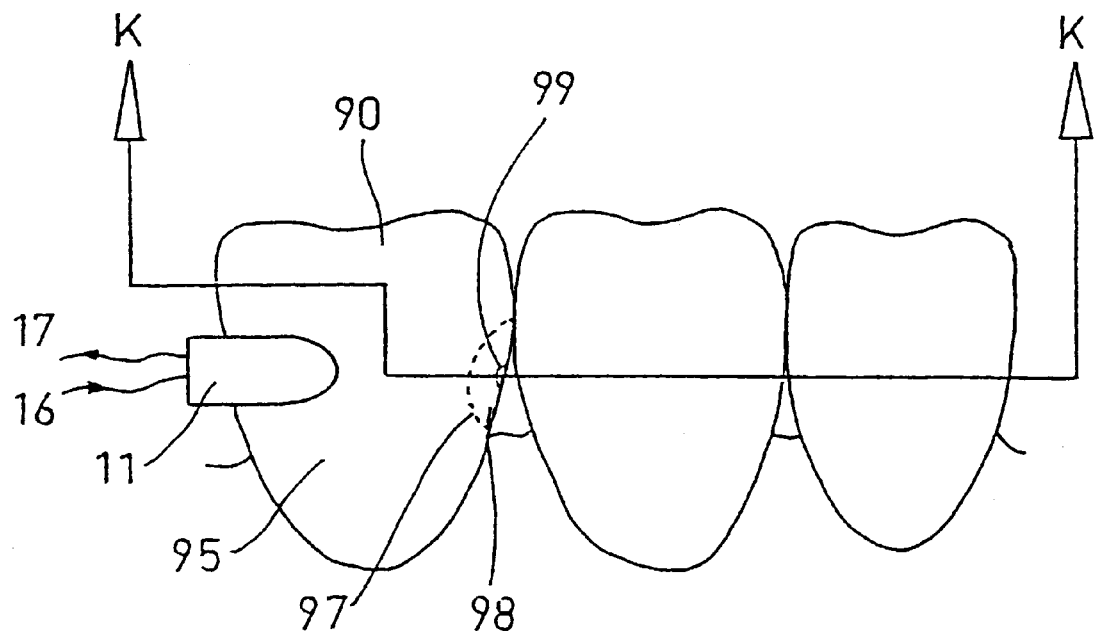
FIG. 13 shows in side view a portion of a dentition, with the probe of FIG. 10 in contact with the crown surface of a tooth.
Figure 14:
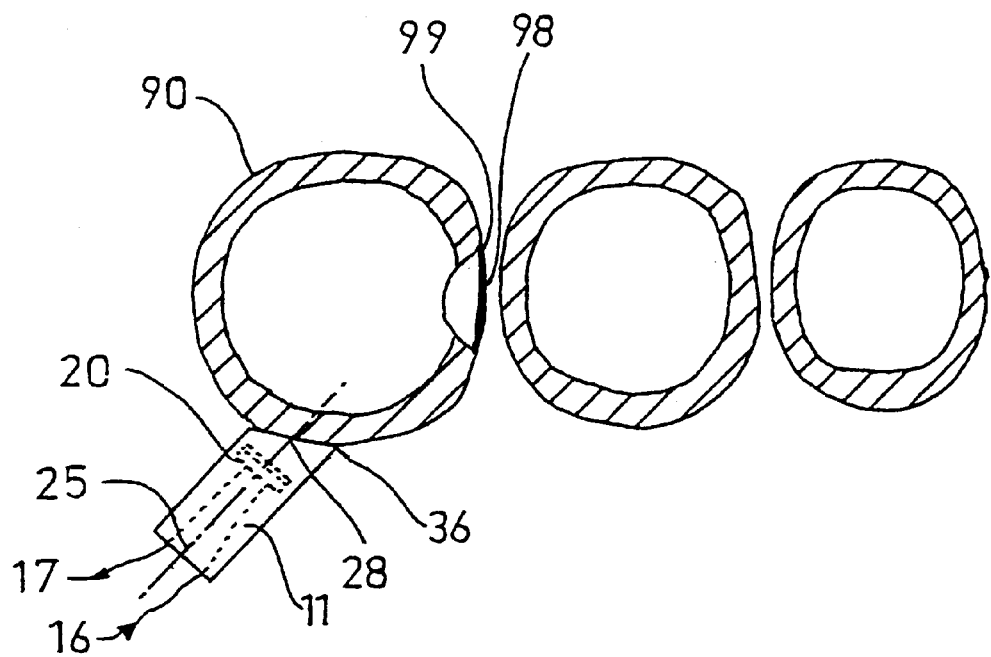
FIG. 14 is cross sectional view of the items shown in FIG. 13 taken along K—K, which represents a coronal section at the level of an interproximal caries lesion.

FIGS. 11 to 14 show a section of a dentition comprising a number of adjacent teeth, wherein surface lesions (99) such as primary or secondary dental caries or a surface crack on the enamel is suspected in an interproximal site (98) of the tooth crown surface (95) of a tooth (90). In FIGS. 11 and 12, the first, second, third, fourth, fifth, sixth, seventh, eighth or ninth embodiment of the probe (10) is illustrated, while in FIGS. 13 and 14, the tenth embodiment of the probe (11) is illustrated.

According to the present invention, when said contact surface (35) in at least partial contact at the intersection of said central longitudinal axis (25), or in the case of focused transducers, the intersection of the principal axis of the focusing element of the corresponding focused transducer, therewith, i.e. at (28), with the tooth crown surface (95) of a tooth (90), ultrasonic waves imparted by means of said coupler (30) onto said tooth crown surface (95) migrate as surface ultrasonic waves along said tooth crown surface (95), departing the said contact surface (35) generally from the leading edge (36) and in the general direction of said major axis (38). In particular with respect to the third to ninth embodiments of the present invention, the said ultrasonic waves generated by the transducer are at least partially focused within the said coupler (30) prior to being imparted onto the tooth crown surface as surface ultrasonic waves. Said lesions (99), if present, are identifiable as surface ultrasonic wave reflections produced thereat. These reflections are received by said ultrasonic transducer (20) and are converted to corresponding electrical signals, which process is well known in the art.

As already described, the surface waves depart from said contact surface (35) generally from the leading edge (36) and in the general direction of said major axis (38), i.e., also parallel to said major transverse plane (31). Any reflected ultrasonic surface waves produced at a surface lesion is generally reflected back to the probe along this direction. Thus, the probe (10) may be oriented on a tooth surface to impart surface waves in a preferred direction. In the preferred embodiment, the probe (10) further comprises identifying means whereby the probe (10) may be suitably oriented with respect to a zone (97) on the said tooth crown surface (95) for substantially directing the ultrasonic surface waves generated by said probe (10) towards said zone (97). Ultrasonic surface wave reflections at maximum amplitude will thus be typically obtained along the said major transverse plane (31). Preferably, said identifying means comprises a suitable targeting mark (50) on said probe (10) or housing (22). Examples of a said targeting mark (50) include an arrow or coloured spot on the outer surface of the said coupler (30), preferably on the said shell (170), comprising said forward portion (32) of said contact surface (35), i.e. preferably close to the said leading edge (36). Thus, a user's task of orienting the probe (10) on the surface (95) of a tooth (90) with respect to a zone (97) is greatly facilitated by being able to direct the targeting mark (50) towards the desired zone (97). In general, said zone (97) is located in the interproximal site (98), though it may be located elsewhere on said tooth crown surface (95).

Figure 15A:
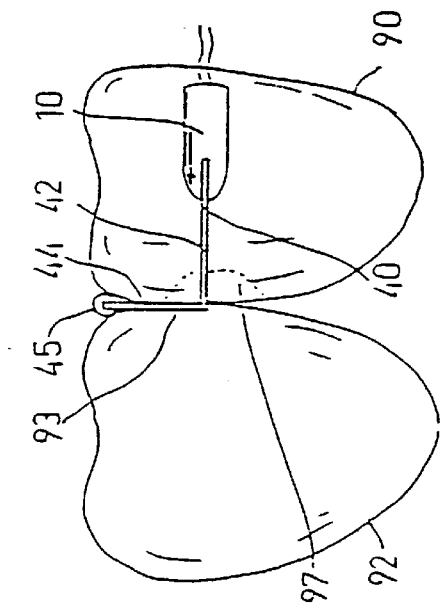
FIG. 15 illustrates schematically the probe of FIG. 10, further comprising adjunct spacing means according to the present invention.
Figure 15B:
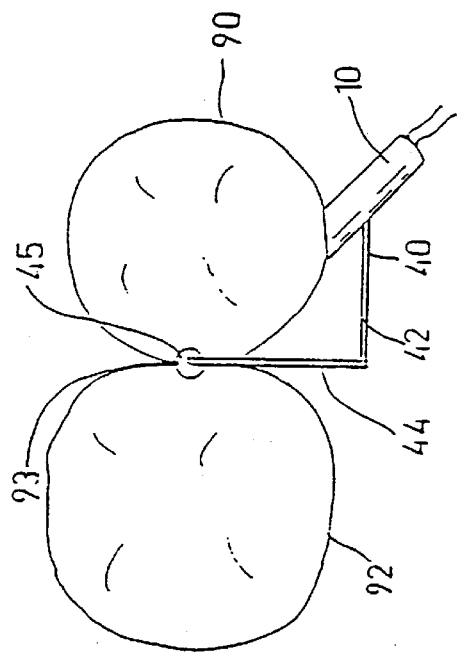
Figure 15C:
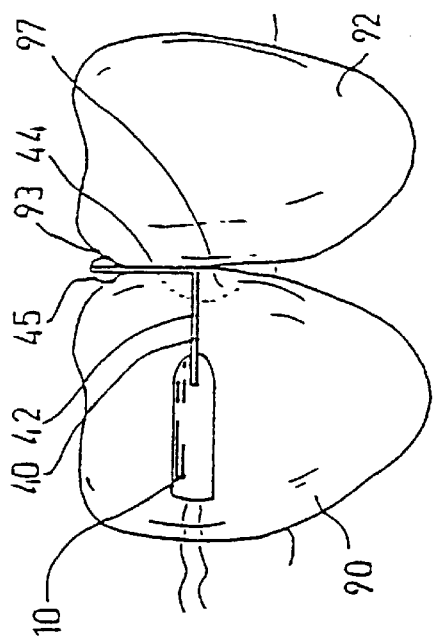
Figure 15D:
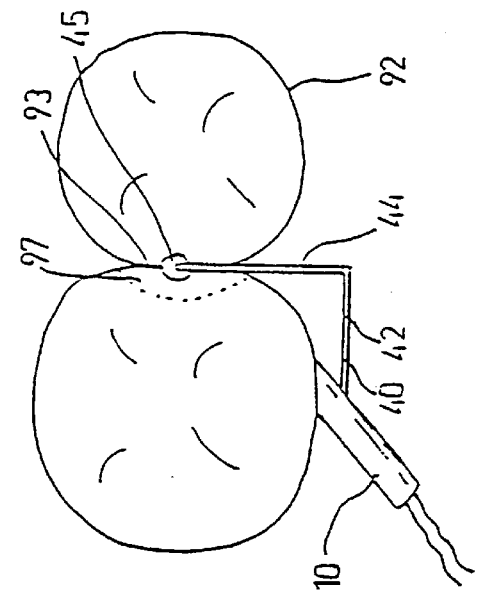

Said identifying means may alternatively or additionally comprise suitable adjunct spacing means (40) placed against the contact point between the examined interproximal surface and an adjacent tooth, for providing a predetermined spatial relationship between said probe and said zone (97). FIG. 15 illustrates, for the tenth embodiment, an example of said spacing means (40), comprising a horizontal spacing member (42) rigidly attached at one end thereof to said probe (11) in proximity to said leading edge (36) thereof, the other end of said spacing member (42) being rigidly attached to a transverse member (44) at one end thereof. Said member (44) is suitably shaped so that the other end (45) thereof may hook onto or press against the contact point (93) between said tooth (90) and an adjacent tooth (92), such that no part of said members (42) or (44) are in contact with the tooth surface (95) anywhere close to an imaginary direct line between said leading edge (36) and said desired zone (97). An operator would thus place the said end (45) of the spacing means (40) against the contact point (93) between two teeth, the said probe (11) being automatically oriented on one tooth thereof towards the corresponding desired zone (97). Optionally, said spacing means (40) may be left-handed, as shown in FIGS. 15(a) and 15(b), or right-handed, as shown in FIGS. 15(c) and 15(d). Preferably, though, said transverse member (44) may be modified, as for example by incorporating a hinging means about its contact point with said horizontal member (42), so that the spacing means may be used alternately either in the right-handed sense or in the left-handed sense.

The present invention also relates to a device for the detection of smooth surface lesions of a tooth crown surface comprising the said probe (10) or (11), as hereinbefore described with respect to the said first, second, third, fourth, fifth, sixth, seventh, eighth or ninth embodiment, and said tenth embodiment, respectively, said device optionally further comprising the optional features as described herein and with reference to the appended Figures.

Figure 16:
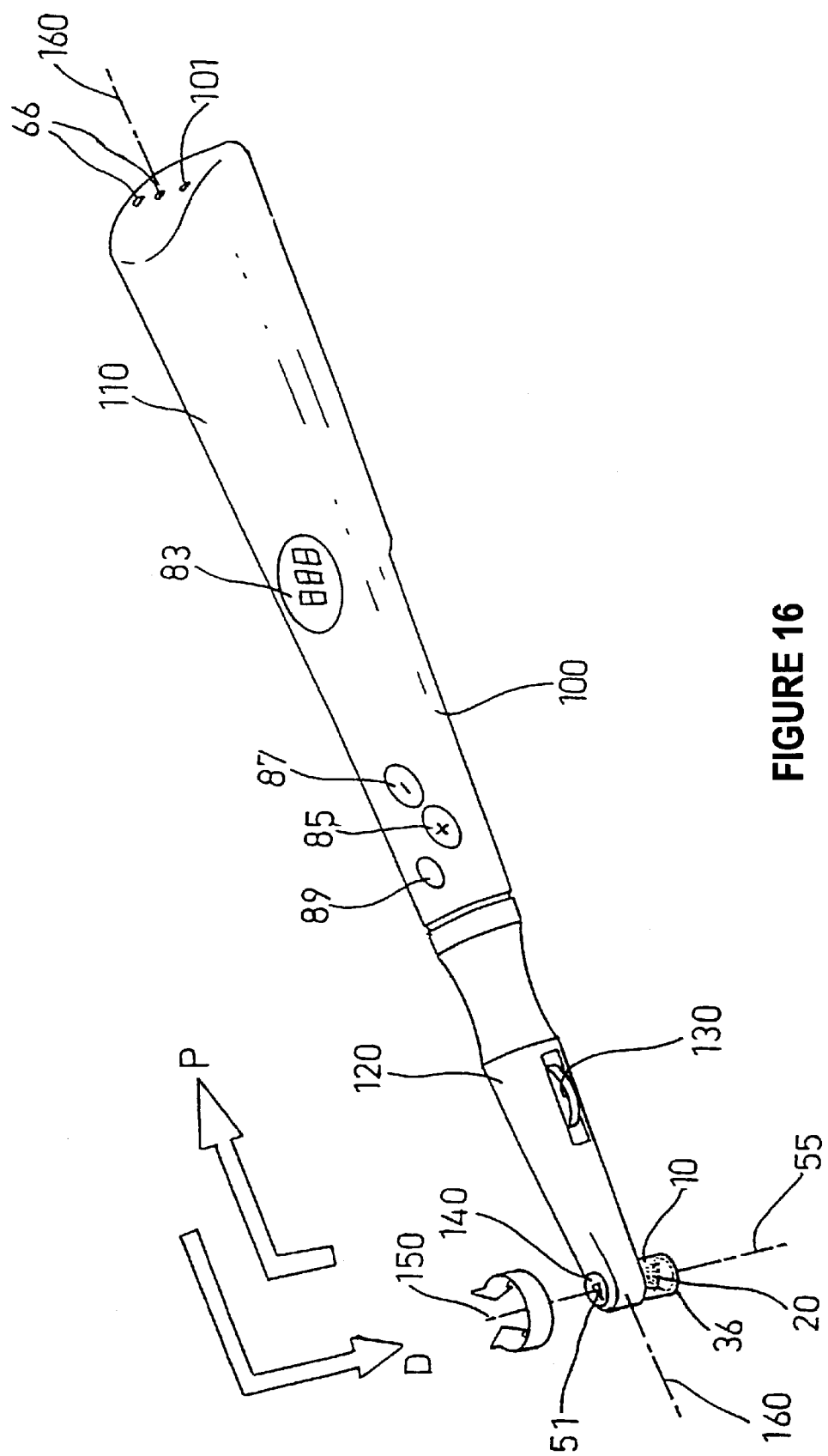
FIG. 16 illustrates schematically the device according to the present invention comprising the probe of FIGS. 1 to 9 incorporated.

The probe (10) is thus preferably housed in a rotatable head (140) located at the distal end of an operator extension handle (100) and releasably or integrally attached thereto, as illustrated in FIG. 16. The longitudinal axis (55) of the housing (22) is substantially parallel and preferably coaxial with the axis of rotation (150) of the said rotatable head (140). The probe (11) according to the second embodiment of the present invention may similarly be integrally or releasably attached to said handle (100) via said rotatable head (140). Preferably, the angle between the said axis of rotation (150) and the longitudinal axis (160) of the handle (100) is approximately 90°, though it may optionally be greater or less than 90°. The handle (100) is of a generally elongate form having a proximal gripping end (110), which may be conveniently configured to house peripheral electronic and/or electrical components are hereinafter described, for example. The distal end (120) of the handle (100) preferably further comprises a rotating mechanism for enabling the said head (140), and therefore the said probe (10), to be rotated at least 180°, though preferably at least 330°, about its longitudinal axis (55) by means of a suitable lever (130) such as a rotatable knob. The rotatable head (140) enables a user to investigate the mesial and distal interproximal sites of each tooth without significantly altering the position of the handle, and therefore the user's position, relative to the patient. (The term "distal interproximal site" herein refers to the interproximal site of a tooth furthest from the midline of the tooth arch, while the term "mesial interproximal site" refers to the opposite interproximal site of the tooth, closer to the said midline). With the leading edge (36) of the probe pointing distally with respect to the handle, the user can investigate one interproximal site of any given tooth; by rotating the probe (10) by about 180° as hereinbefore described, the leading edge (36) is now pointing proximally with respect to the handle (100), and may therefore be used to investigate the other interproximal site of the same tooth. In the preferred embodiment, said targeting mark (50) comprises a suitably coloured arrow (51) on the said rotatable head (140), preferably orthogonal to said axis of rotation (150), wherein the arrow points in the direction of the leading edge (36) and thus rotates together with the head (140) and probe (10). Preferably, said arrow (51) may further comprise a suitable light source, optionally also arrow-shaped, for example suitably connected to said battery (65), for further aiding the user in determining the location of the leading edge (36) of the probe (10) with respect to the user.

Preferably, at least the distal end (120) of the handle (100) is autoclavable, in particular the portion of said distal end (120) that is in contact with and/or which enters the patient's oral cavity.

Figure 17:
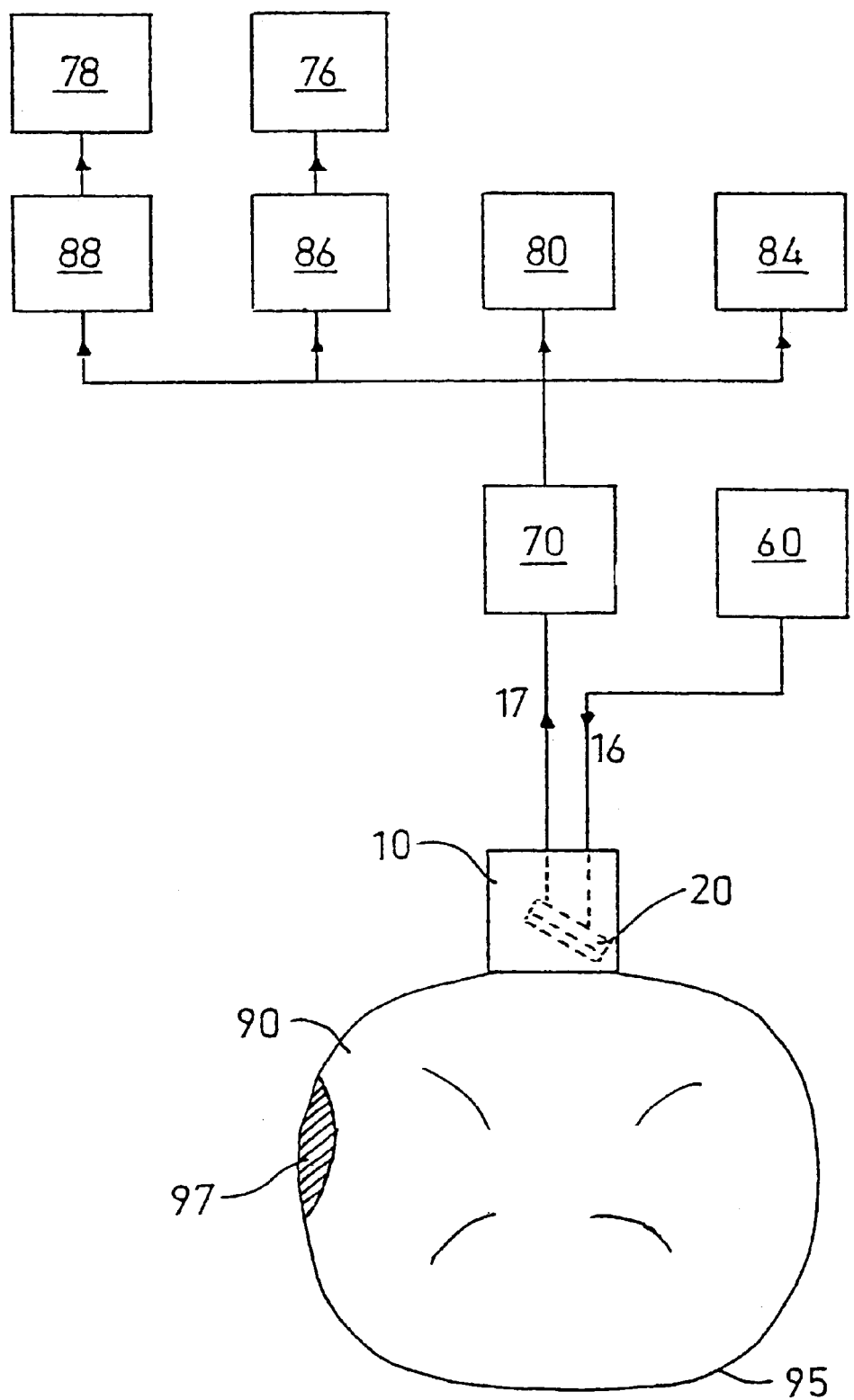
FIG. 17 illustrates schematically the probe of FIGS. 1 to 9 together with peripheral electrical and/or electronic components.
Figure 18:
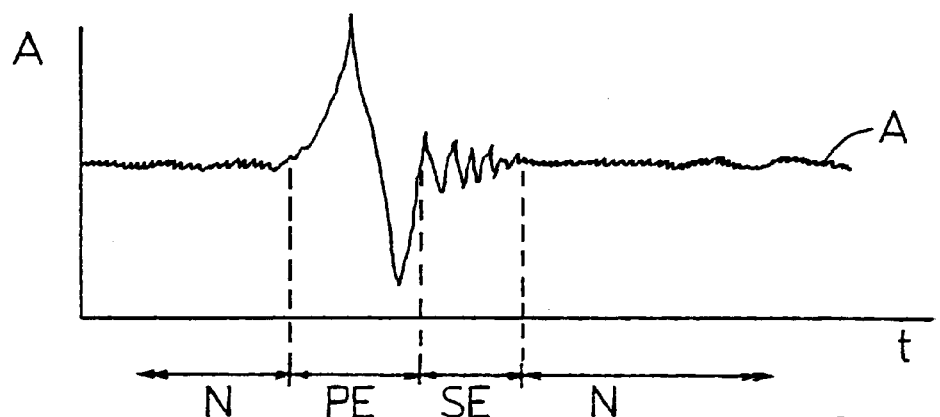
FIG. 18 illustrates schematically a typical A-scan of surface ultrasonic wave reflections that may be received by the probe of the present invention.

Said probe (10) may be suitably interconnected to peripheral electronic and/or electrical components. While FIG. 17 illustrates schematically one example of the relationship between said probe (10) and peripheral components for at least some of the corresponding embodiments of said probe (10), the same relationships may apply to the probe (11) according to the tenth embodiment of the present invention, mutatis mutandis. A signal generator (60) comprising a suitable power source is electrically connected to said transducer (20), which is then able to impart ultrasonic surface waves along the surface (95) of the tooth (90) as hereinbefore described. Surface waves reflections received by said transducer, basically comprising a fluctuation of amplitude "A" of the received ultrasonic wave reflection with respect to time-of-flight "t", for example, as illustrated in FIG. 18, are converted into corresponding electrical signals which are then amplified and processed in a processor (70). Peripheral electronic means such as oscilloscope (80) is operatively connected to said probe (10) and may be used for displaying the profile of said surface ultrasonic wave reflections received by said probe (10) in a manner known in the art. Said electrical signals may also be channeled to an electronic computer (84) for further analysis. The said oscilloscope (80) may typically display a sequence of echoes of varying amplitude, "A", as a function of time-of-flight, "t", hereinafter referred to as an A-scan. Time-of-flight relates to a time-separation on the display which may be equated to velocity and therefore real distance along the tooth surface (95). This form of display is relatively easy to interpret by a user, typically a dentist for example, as the occurrence of an echo of substantial amplitude at a particular time-of-flight, relative to amplitude levels of background noise (N) at other times-of-flight, indicates the existence of a lesion (99) at a distance along the tooth surface from the probe (10) corresponding to this time-of-flight.

Figure 19:
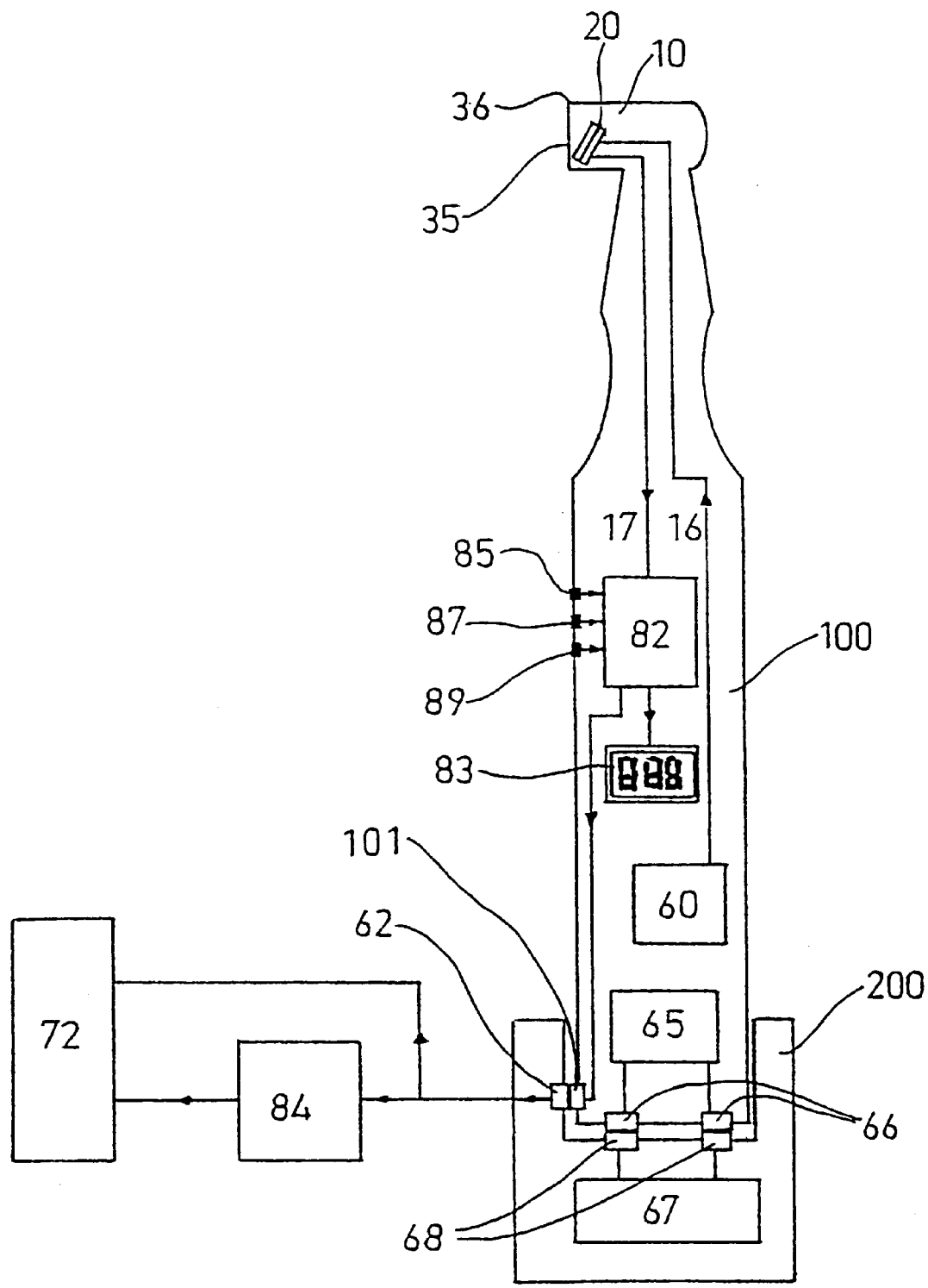
FIG. 19 illustrates the device of FIG. 16 together with peripheral electrical and/or electronic components.

Alternatively, the probe (10) is preferably suitably interconnected to peripheral electronic and/or electrical components preferably accommodated in said handle (100), as shown schematically in FIG. 19. A signal pulser (60) is electrically connected to said transducer (20), which is then able to impart ultrasonic surface waves along the surface (95) of the tooth (90) as hereinbefore described. Surface waves reflections received by said transducer are converted into corresponding electrical signals which are then amplified and processed in a microprocessor (82). The said microprocessor (82), operatively connected to said transducer (20), can store and/or analyse the electrical signals generated by the said transducer corresponding to the ultrasonic surface wave reflections received at the transducer (20). The device, or the said microprocessor (82), may optionally further comprise means for providing electronic communication between said microprocessor (82) and at least one electronic component external thereto. Said electronic communications means may comprise, for example, an output (101) for channeling data to an external electronic device as hereinafter described. The said handle (100) optionally further comprises a suitable electronic display means accommodated therein and visible to the user. Said electronic display means, such as an LCD display (83), for example, is operatively connected to said microprocessor (82) and may be used for displaying alphanumeric characters, or symbols corresponding to such characters, such as for example a numeric value correlated by the microprocessor (82) to the size/depth and/or type of the lesion encountered by the surface waves. This form of display is particularly easy to interpret by a user. The microprocessor (82) may also be programmed to distinguish between primary enamel caries primary dentinal caries, secondary caries and tooth crown surface cracks, as hereinafter described. The display (83) may also be used to display other data such as the approximal site number (input by the user via switches (85), (87) and (89), as hereinafter described) of the tooth being examined.

In the preferred embodiment, the said handle (100) further comprises input switches operatively connected to the said microprocessor (65) for enabling the user to label the results obtained in any particular test. Preferably, such labels comprise suitable alphanumeric characters for identifying the approximal site number, for example, and three input switches are comprised in the said handle: a scroll up switch (85), a scroll-down switch (87) and a reset switch (89), enabling the user to suitably label the results of each test with appropriate alphanumeric characters, for example. These labels may then be stored by the microprocessor (82) and eventually downloaded to computer (84) or printed at printer (72) together with the results of each corresponding test.

Said signal pulser (60), microprocessor (82) and display are preferably accommodated in said handle (100). The handle (100) optionally further comprises a suitable electrical supply for providing the necessary electrical needs of the probe (10) and the peripheral electrical and electronic components comprised in said handle (100), preferably a rechargeable battery (65) accommodated in the handle (100) and having external contacts (66) for recharging. Optionally, the handle (100) may be conveniently stored when not in use on a base (200), which may be desk-top or wall mounted, for example. The base (200) preferably comprises a battery charger (67), suitably connected to an external electrical supply, and having electrical contacts (68) complementary to said contacts (66), for enabling the battery (65) to be recharged. Alternatively, the handle may comprise an induction recharging system for the battery (65), and thus does not require the said contacts (66), in which case, the said base (200) comprises a compatible induction recharger. The base (200) may further optionally comprise a suitable contact (62), complementary to output (101), and operatively connected to an external electronic component such as a computer (84) and/or a printer (72), enabling the data processed by the microprocessor (82) to be downloaded to the computer (84) for further processing, or directly to the printer (72) for printing.

Figure 20A:
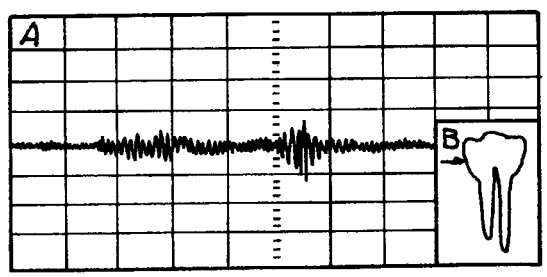
FIG. 20 illustrates typical A-scans of surface ultrasonic wave reflections obtained with teeth having caries lesions of various depths.
Figure 20B:
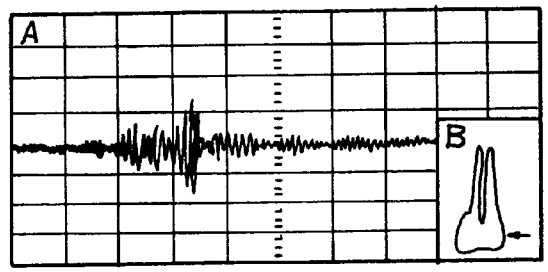
Figure 20C:
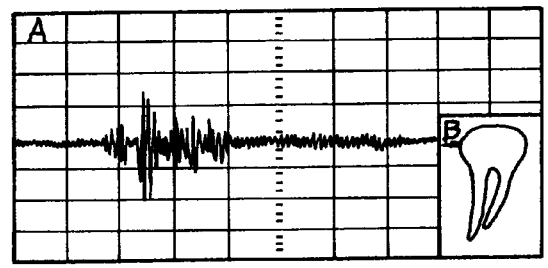
Figure 20D:
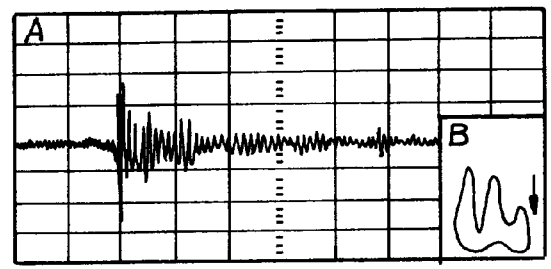
Figure 20E:
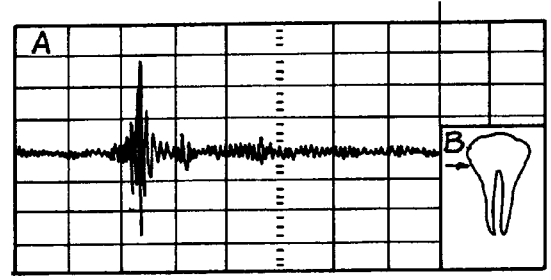
Figure 20F:
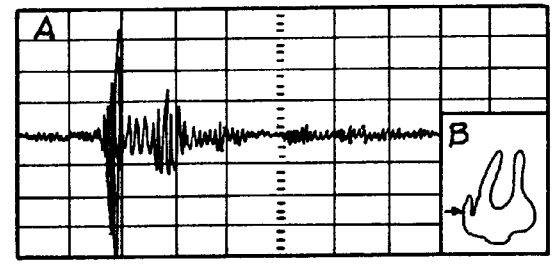

The amplitude of reflected ultrasonic waves from lesions may be correlated with the depth of caries lesions. FIGS. 20(a) to 20(f) shows the A-scans that were obtained by using a probe (10) according to the present invention on six teeth having varying degrees of caries lesions. FIG. 20(a) relates to a tooth having a small whitespot lesion; FIGS. 20(b) and 20(c) relate to a whitespot and a white-and-brownspot lesion; FIGS. 20(d), 20(e) and 20(f) relate to caries lesions with surface cavitation.

Table I tabulates the amplitudes of the reflected ultrasonic surface waves relating to FIGS. 20(a) to 20(f), and also shows corresponding radiolucency produced by interproximal caries on each tooth, said radiolucency being scored according to the German Rating System (GRS) [Marthaler T. M., (1970) Caries Res, 4: 224–242] as follows:

0: no radiolucency evident
1: radiolucency limited to outer one half of enamel
2: radiolucency evident in inner one half of enamel
3: radiolucency evident in outer one half of dentine
4: radiolucency penetrates into inner one half of dentine

TABLE I

Ultrasonic and radiographic scores of caries lesion relating to FIGS. 20(a) to 20(f)

| FIG. No. | Echo amplitude (mV) | Radiolucency extent (GRS) |
|---|---|---|
| 20(a) | 62 | 0 |
| 20(b) | 152 | 2 |
| 20(c) | 176 | 2 |
| 20(d) | 240 | 3 |
| 20(e) | 292 | 3 |
| 20(f) | 380 | 3 |

Thus, it is possible to construct amplitude bands, each having an upper and a lower threshold level, wherein each band corresponds to a radiolucency extent, which in turn relates to the extent of caries lesion.

Optionally, then, the said probe (10) further comprises first electronic selection means (86), suitably connected thereto, for generating electronic signals corresponding to surface ultrasonic wave reflections having an amplitude within at least one set of predetermined upper and lower thresholds in a manner known in the art. Said differently, said selection means (86) acts as a filter and generates a discrete electronic signal corresponding to a particular amplitude band when the amplitude of a surface ultrasonic wave reflection falls within said band. In the preferred embodiment, the functions of said first electronic selection means (86) may be incorporated in the said microprocessor (82). Said microprocessor (82) may then display a numeric character or a symbol on said display (83) such as "0", "1", "2" etc. according to whether the signal generated by said selection means of the microprocessor (65) corresponds to an amplitude band having a similar value of radiolucency extent correlated thereto. In other embodiments comprising said selection means (86) as a separate component, for example as illustrated in FIG. 17, said selection means (86) may further comprise visual and/or audio display means (76) for displaying said electronic signals in a manner known in the art such as a LCD counter wherein the numbers "0", "1", "2" etc. may be similarly displayed according to whether the signal generated by said selection means (86) corresponds to an amplitude band having a similar value of radiolucency extent correlated thereto.

The characteristics of the reflected ultrasonic wave may be conveniently correlated to the type and extent of surface lesion that produces the reflection. A reflected ultrasonic wave typically comprises at least a primary echo (PE) and a secondary echo (SE), both having amplitudes substantially greater than the general background level $A_n$ of noise (N), as illustrated in FIG. 18. The primary echo is generally characterised by having a larger amplitude than the secondary echo, and the two echoes are substantially consecutive. The secondary echo is generally before and/or after the primary echo. The said microprocessor (82) may optionally by programmed to analyse the characteristics of the reflected ultrasonic wave and to display one or more alphanumeric characters or symbols on the said display (83) relating to the type of surface lesion that has been encountered, as well as the extent of same in some cases, according to suitable preprogrammed correlations, e.g., as hereinbefore described in reference to Table I.

For example, caries lesions confined to the enamel, hereinafter "enamel caries", produce surface wave reflections wherein the range of maximum amplitude of the primary echo thereof, i.e., the primary echo amplitude band, is substantially below the corresponding primary echo amplitude bands obtained with ultrasonic wave reflections produced at a tooth crown surface crack or at a site having dentinal caries, i.e., caries lesions that extend to the dentine. Thus, it is possible to distinguish enamel caries from both tooth crown surface cracks and from dentinal caries.

Dentinal caries and tooth crown surface cracks may produce ultrasonic wave reflections having similar or overlapping primary echo amplitude bands. In order to distinguish between these two types of surface lesions, the characteristics of the whole signal, including the primary echo and the secondary echo, may also be advantageously analysed and typically expressed as the RMS (Root Mean Square) value of the signal, i.e., of the primary and secondary echo. The characteristics of the reflected wave may then be expressed as a function F1 of the primary echo amplitude and of the RMS value of the signal. For example, the function F1 may be the ratio of primary echo amplitude to said RMS value. Alternatively, the function F1 may take other forms. The function F1 may be advantageously chosen so that the range of values for F1 obtained with ultrasonic wave reflections produced at tooth crown surface cracks is sufficiently distinguishable from the corresponding range of values obtained for reflections produced at sites comprising dentinal caries.

The presence of secondary caries at the gingival margin of an interproximal class II restoration may be determined in a similar manner. A class II restoration at an interproximal site will be immediately obvious to a skilled user, such as a dentist for example. The presence of such a restoration suggests testing for the presence of secondary caries at the interproximal margin of the said restoration. An intact filing on the gingival margin will generally produce an ultrasonic surface wave reflection having a low signal in relation to the general levels of background noise, while a much higher signal is produced by secondary caries at such a site. However, a class II restorations are seldom perfect, there is a need to distinguish a secondary caries lesion at the gingival margin from an underfilling or overfilling at the interproximal site, when using the probe of the present invention, as such underfillings or overfillings also produce ultrasonic wave reflections having a relatively high signal.

For this purpose, the characteristics of the primary and secondary echoes of a reflected ultrasonic surface wave produced at the gingival margin of an interproximal class II restoration may also be advantageously analysed. The characteristics of the reflected ultrasonic surface wave may be expressed as a function F2 of the amplitude of the primary echo and the RMS value of the signal, i.e., of the primary echo together with the secondary echo. For example, the function F2 may be the ratio of primary echo amplitude to the said RMS value. The presence of secondary caries in the gingival margin may be then identified by the value of the function F2, since the value of F2 thus defined is lower for reflected ultrasonic waves produced at secondary lesions than at overfillings or underfillings adjacent to the gingival margin of an interproximal class II restoration site. As with F1, the function F2 may alternatively take other forms. The function F2 is advantageously chosen so that the range of values for F2 obtained with ultrasonic wave reflections produced at secondary caries lesions at the gingival margins of interproximal class II restoration sites is sufficiently distinguishable from the corresponding range of values obtained for reflections produced at these sites comprising overfillings or underfillings.

Further, it is also possible to construct time of flight bands, each having an upper and a lower threshold level, wherein each band corresponds to a region on the tooth surface (95) at a corresponding distance from the probe (10). Optionally, then, the said probe (10) further comprises second electronic selection means (88), suitably connected thereto, for generating electronic signals corresponding to surface ultrasonic wave reflections having significantly higher amplitude than background levels wherein the time of flight corresponding to said higher amplitude falls within at least one set of predetermined upper and lower thresholds in a manner known in the art. Said differently, said selection means (88) acts as a filter and generates a discrete electronic signal corresponding to a particular time of flight band, and therefore a particular region on the tooth surface, when the amplitude of a surface ultrasonic wave reflection sufficiently higher than background levels falls within said band. Thus an operator such as a dentist, for example, may position said probe (10) at a predetermined distance interval, say 4 mm from a desired zone (97), and, if reflections of ultrasonic waves are detected, said operator may thus ensure that these reflections originate from said zone, as the said selection means (88) would be set to generate a discrete signal when the time of flight of the reflected waves corresponding to, say, 3.5 mm–4.5 mm. The precise upper and lower threshold levels for said time of flight bands may differ for different types of teeth, e.g. molars incisors and canines. Preferably, the functions of the said second electronic selection means (88) are incorporated in the said microprocessor (82). Said microprocessor may then display the characters "M", "I", "C" etc. on said display (83) according to whether the signal generated by said selection means of the microprocessor (65) corresponds to a standard time of flight expected on the type of tooth being tested. In other embodiments comprising said means (88) as a separate component, for example as illustrated in FIG. 17, said second selection means (88) may further comprise visual and/or audio display means (78) for displaying said electronic signals corresponding to each type of tooth in a manner known in the art such as a LCD counter wherein the characters "M", "I", "C" etc. may be similarly displayed according to whether the signal generated by said selection means (88) corresponds to a standard time of flight expected on the type of tooth being tested. Optionally, the said selection means (88) may be preset by the user according to a preferred set of upper and lower threshold levels for time of flight.

The probe (10) may optionally further comprises a suitable extension handle (15) releasably attached to or integral with said probe (10), as illustrated in FIG. 21 for the second embodiment of the present invention. Said handle (15) may be similar to handles known in the art and used by dentists to reach deep molars. Said handle (15) is preferably made from a rigid medically compatible material such as stainless steel or a suitable plastic material, examples of which are known in the art, and is preferably hollow to allow input and output cables, (16) and (17) respectively, to said transducers (20) to be routed therein.

Figure 21A:
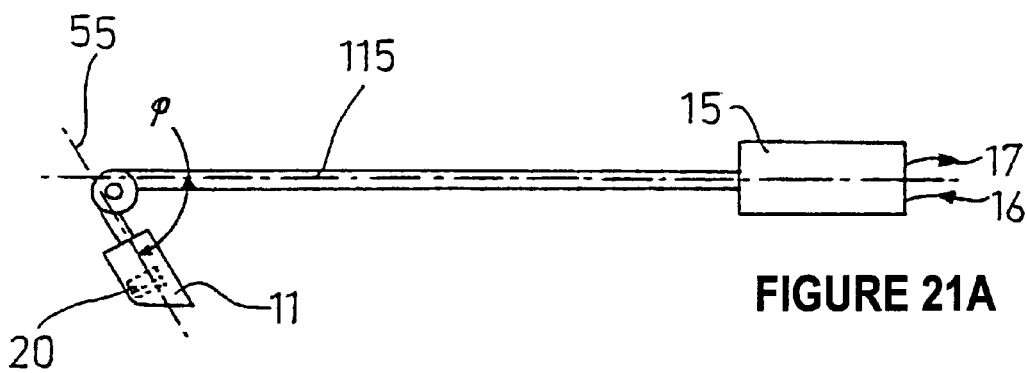
FIG. 21 shows the probe of FIG. 10 fitted with an extension handle according to the present invention.

Optionally, said handle (15) is mounted to said probe (10) via suitable hinge means (12), wherein the said handle (15) may rotate relative to said probe (10) varying the angle φ between the said longitudinal axis of the housing (55) and the longitudinal axis (115) of the handle (15), as illustrated in FIG. 21(a), wherein angle φ may be an acute or an obtuse angle. Said hinge means (12) are known in the art and may comprise a two-dimensional hinge or a universal joint, for example.

Figure 21B:
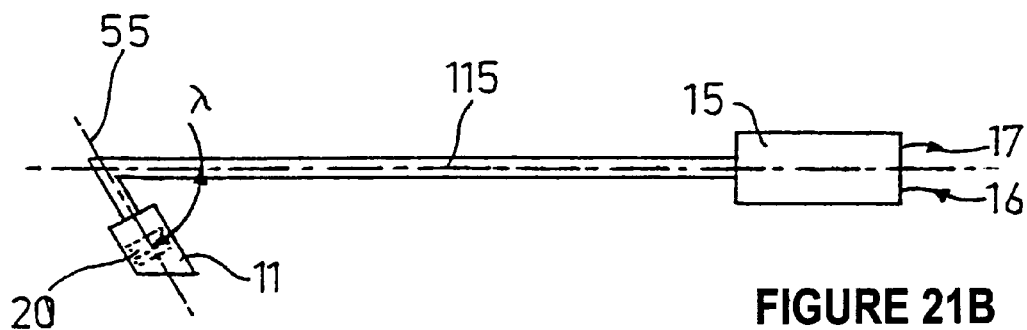
Figure 21C:
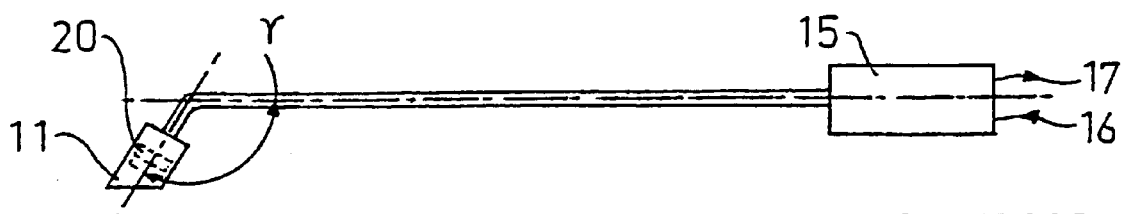

Optionally, said probe (10) may be mounted at an acute angle λ or alternatively at an obtuse angle γ relative to said handle (15), as illustrated in FIGS. 21(b) and 21(c) respectively.

The present invention also relates to a method for the detection of smooth surface lesions of a tooth crown surface, comprising the steps of:

(i) providing a probe comprising an ultrasonic surface wave generator and an ultrasonic surface wave receiver;

(ii) positioning said probe in substantial contact with a tooth crown surface such that ultrasonic surface waves may be imparted by said ultrasonic surface wave generator onto said tooth surface;

(iii) generating and imparting ultrasonic surface waves by said ultrasonic surface wave generator onto said tooth crown surface, said surface ultrasonic waves migrating along said tooth crown surface;

(iv) detecting said lesions as surface ultrasonic wave reflections produced thereat and received by said ultrasonic surface wave receiver.

The present invention also relates in to a method for the detection of smooth surface lesions of a tooth crown surface, comprising the steps of:

(i) providing a probe comprising an ultrasonic surface wave generator capable of transmitting surface ultrasonic waves along a tooth crown surface and an ultrasonic surface wave receiver capable of receiving ultrasonic surface wave reflections produced at smooth surface lesions that may be present on said tooth surface;

(ii) positioning said probe in substantial contact with a tooth crown surface such that ultrasonic surface waves may be imparted by said ultrasonic surface wave generator onto said tooth surface; wherein (iii) said ultrasonic surface wave generator can generate surface ultrasonic waves onto said tooth crown surface, said surface ultrasonic waves migrating along said tooth crown surface; and (iv) said ultrasonic surface wave receiver receives ultrasonic wave reflections produced at surface lesions present on said surface, thereby detecting said lesions.

Optionally, said ultrasonic surface wave generator and said ultrasonic surface wave receiver are unitary.

The present invention relates in particular to a method for the detection of smooth surface lesions of a tooth crown surface, comprising the steps of:

(i) providing a probe (10) or (11) and/or said device, substantially as hereinbefore described with reference to the various embodiments and optional features thereof, and with reference to the attached Figures, in particular comprising said focused transducer;

(ii) positioning said contact surface (35) in substantial contact with a tooth crown surface at least at said intersection of said principal axis of said focusing element of said transducer with said contact surface; wherein (iii) said probe can generate at least partially focused surface ultrasonic waves onto said tooth crown surface, said surface ultrasonic waves migrating along said tooth crown surface; and (iv) said probe receives at least some ultrasonic wave reflections produced at surface lesions present on said surface, thereby detecting said lesions.

In particular, the ultrasonic surface wave reflections produced by said lesions and received at said transducer (20) may be represented as a corresponding A-scan, comprising at least a primary echo and a secondary echo, substantially as hereinbefore described.

Thus, the probe (10), may be used as follows. A user positions the probe (10) (or probe (11), mutatis mutandis) onto the crown surface (95) of a tooth (90), preferably with the aid of said handle (100) (or alternatively said handle (115)), ensuring that the contact surface (35) is in at least partial contact with the surface (95) preferably at intersection (28) of the principal axis of the focusing element of the focused transducer with said contact surface (35). The leading edge (36) of the coupler (30) is then oriented towards the zone (97) where caries lesions are suspected, usually the interproximal site (98), but may be elsewhere on the tooth crown surface (95). The user may be optionally aided in orienting the probe (10) by means of a target (50) or adjunct spacing means (40), as hereinbefore described. Ultrasonic waves are then generated by the transducer (20) in a manner known in the art. In the third to ninth embodiments, the corresponding focusing elements at least partially focus the ultrasonic waves in the direction of the corresponding principal axes, at least within the said coupler (30). The at least partially focused ultrasonic waves are then imparted to the tooth surface (95) typically as at least partially focused surface ultrasonic waves by means of the corresponding coupler (30). The ultrasonic surface waves migrate along the surface generally towards the zone (97), and if they encounter a lesion (99), ultrasonic surface wave reflections are produced thereat. These ultrasonic surface wave reflections are then received by the transducer (20) and may then be processed and/or analysed and/or displayed and/or selected as hereinbefore described to identify to the user the presence of a lesion, and, optionally, to indicate the size/depth and/or the type of lesion detected. In particular, the at least partially focused ultrasonic waves obtained with the third to ninth embodiments enhances sensitivity and enable small lesions to be identified.

Optionally, enamel caries lesions may be distinguished from dentinal caries lesions or tooth crown cracks, as hereinbefore described. Thus, the method for so distinguishing comprises the steps of:

(I) comparing the amplitude of the said primary echo with the range of primary echo amplitudes normally obtained for dentinal caries lesions and tooth crown surface cracks; and (II) identifying said lesion as an enamel caries lesion if said amplitude of said primary echo corresponding to said reflected ultrasonic surface waves is substantially lower than the said range of primary echo amplitudes normally obtained for dentinal caries lesions and tooth crown surface cracks; or (III) identifying said lesion as a dentinal caries lesion or a tooth crown surface crack if said amplitude of said primary echo corresponding to said reflected ultrasonic surface waves is substantially lower than the said range of primary echo amplitudes normally obtained for dentinal caries lesions and tooth crown surface cracks.

Optionally, dentinal caries lesions may be distinguished from tooth crown surface cracks, as hereinbefore described. Thus, the method for so distinguishing comprises the steps of:

(I) determining the amplitude of the said primary echo and the RMS value of the said primary echo and the said secondary echo corresponding to said ultrasonic surface wave reflections, and incorporating the said primary echo amplitude and the said RMS value in a function F1 representing the said ultrasonic surface wave reflections (II) comparing the value of the function F1 obtained for said ultrasonic surface wave reflections in (I) with the range of values of the function F1 normally obtained for dentinal caries lesions and for tooth crown surface cracks; and (III) identifying said lesion as a dentinal caries lesions or as a tooth crown surface crack depending on whether the value of function F1 is within the range of values of the function F1 normally obtained for dentinal caries lesions or for tooth crown surface cracks, respectively.

In particular, said function F1 is the ratio of the amplitude of said primary echo to the RMS value of the said primary echo and the said secondary echo corresponding to said reflected ultrasonic surface waves, as hereinbefore described.

Optionally, secondary caries lesions at the gingival margin of an interproximal class II restoration may be distinguishable from imperfections of said restoration, as hereinbefore described. Thus, the method for so distinguishing comprises the steps of:

(I) determining the amplitude of the said primary echo and the RMS value of the said primary echo and the said secondary echo corresponding to said ultrasonic surface wave reflections produced at said gingival margin, and incorporating the said primary echo amplitude and the said RMS value in a function F2 representing the said ultrasonic surface wave reflections;

(II) comparing the value of the function F2 obtained for said ultrasonic surface wave reflections in (I) with the range of values of the function F2 normally obtained for secondary caries lesions and for class II restoration imperfections at the gingival margin; and (III) identifying a said secondary caries lesion or a class II restoration imperfection at the class II gingival margin depending on whether the value of function F2 is within the range of values of F2 normally for secondary caries lesions or for class II restoration imperfections, respectively.

Preferably, function F2 is the ratio of the amplitude of said primary echo to the said RMS value of the said primary echo and said secondary echo corresponding to said reflected ultrasonic surface waves, as hereinbefore described.

Although only a few embodiments and optional features thereof have been described in detail in the foregoing description, the present invention is not limited thereto and is only defined by the scope of the claims.

What is claimed is:

1. A probe for the detection of smooth surface lesions of a tooth crown surface, comprising an ultrasonic transducer, capable of transmitting ultrasonic waves and receiving ultrasonic wave reflections via a distal face thereof, and further comprising a coupler operatively connected to said distal face of said transducer and having a contact surface distal to said transducer, wherein said transducer is a focused transducer comprising at least one focusing element capable of at least partially focusing ultrasonic sound waves generated by said transducer along a principal axis of the said focusing element at least within said coupler, said coupler comprising a wedge angle B between a plane substantially perpendicular to the said principal axis of the said focusing element and a plane substantially tangential to the said contact surface at least at the intersection of said principal axis with said contact surface, said wedge angle B being substantially different from 0°, whereby, when said contact surface is in substantial contact with a tooth crown surface at least at said intersection of said principal axis with said contact surface, ultrasonic waves generated by said ultrasonic transducer are imparted by said coupler onto said tooth crown surface as surface ultrasonic waves which migrate along said tooth crown surface, said ultrasonic waves being at least partially focused along said principal axis at least within said coupler, and said lesions being detectable as surface ultrasonic wave reflections produced thereat received by said transducer.

2. A probe according to claim 1, wherein said at least one focusing element consists of said distal face of said focused transducer, said distal face being substantially concave with a concavity having an overall curvature at least substantially sufficient to enable ultrasonic waves generated by said transducer to be at least partially focused at least within said coupler.

3. A probe according to claim 2, wherein said concavity is substantially spherical.

4. A probe according to claim 2, wherein said concavity is substantially parabolic in longitudinal cross-sectional profile.

5. A probe according to claim 2, wherein said concavity is substantially cone-shaped.

6. A probe according to claim 1, wherein said distal face of said transducer is substantially planar, and said focusing element comprises a suitable plane-concave lens intermediate said distal face and said contact surface, said plane-concave lens being capable of at least partially focusing ultrasonic waves generated by said transducer, at least within said coupler.

7. A probe according to claim 1, wherein said distal face is substantially planar, and said focusing element comprises a hollow reflecting mirror intermediate said distal face and said contact surface, said reflecting mirror characterised in comprising a distal opening proximal and near to said contact surface, a proximal opening distal and near to said distal face of said transducer, and an inner reflecting converging surface, wherein said inner reflecting converging surface comprises a suitably converging profile at least substantially sufficient as to enable ultrasonic waves generated by said transducer to be at least partially focused at least within said coupler.

8. A probe according to claim 1, wherein said distal face is substantially planar, and said focusing element comprises a suitable phase plate intermediate said distal face and said contact surface, said phase plate being capable of at least partially focusing ultrasonic waves generated by said transducer, at least within said coupler.

9. A probe according to claim 1, wherein said distal face of said transducer is substantially planar, and said focusing element comprises a suitable cone-shaped converging lens intermediate said distal face and said contact surface, said cone-shaped converging lens being capable of at least partially focusing ultrasonic waves generated by said transducer, at least within said coupler.

10. A probe according to claim 1, wherein said at least one focusing element consists of said distal face of said focused transducer, said distal face being substantially cylindrically concave with a concavity having an overall curvature at least substantially sufficient as to enable ultrasonic waves generated by said transducer to be at least partially focused along substantially a principal band at least within said coupler, said cylindrical concavity having a focal line substantially coplanar with the said longitudinal focusing axis.

11. A probe according to claim 1, wherein said principal axis is substantially co-aligned with the longitudinal axis of said transducer.

12. A probe according to claim 1, wherein said angle B is obtained from the equation:

$$B = \sin^{-1}(V_L/V_S) \pm E°$$

wherein $V_L$ is the longitudinal velocity in the coupler material, and $V_S$ is the velocity of surface ultrasonic waves in enamel, and wherein E is between about 0° and about 10°.

13. A probe according to claim 1, wherein said angle B is between 10° and 80°, preferably between 15° and 35°.

14. A probe according to claim 1, wherein said contact surface is substantially planar.

15. A probe according to claim 1, wherein said contact surface is substantially concave.

16. A probe according to claim 1, wherein said coupler is rigid.

17. A probe according to claim 1, wherein said contact surface is elastically distortable.

18. A probe according to claim 17 wherein said coupler is made from polyurethane or silicone or any other suitable material.

19. A probe according to claim 1, further comprising a housing for accommodating said probe.

20. A probe according to claim 19, wherein said housing comprises a housing longitudinal axis which is at an angle δ to said longitudinal axis of said probe, wherein δ is substantially different from 0°.

21. A probe according to claim 20, wherein said angle δ is substantially equal to said overall wedge angle B.

22. A probe according to claim 19, wherein said housing comprises a housing longitudinal axis which is substantially parallel to, and optionally coaxial with, said longitudinal axis of said probe.

23. A probe according to claim 19, wherein said coupler is integral with said housing.

24. A probe according to claim 19, wherein said coupler is a separate component to said housing.

25. A probe according to claim 19, further comprising a protective shell around at least an external portion of said housing and said coupler and excluding said contact surface.

26. A probe according to claim 1, further comprising identifying means whereby said probe may be suitably oriented with respect to a desired zone on said tooth crown surface for substantially directing said surface ultrasonic waves towards said zone.

27. A probe according to claim 26, wherein said identifying means comprise a suitable targeting mark on said housing.

28. A probe according to claim 1, further comprising a suitable extension handle releasably attached to or integral with said probe.

29. A probe according to claim 28, wherein said handle comprises a rotatable distal head for accommodating said probe therein.

30. A device for the detection of smooth surface lesions of a tooth crown surface comprising the probe according to claim 1.

31. A device according to claim 30, further comprising peripheral electronic means, operatively connected to said probe, for displaying the profile of said surface ultrasonic wave reflections received by said device.

32. A device according to claim 30, further comprising first electronic selection means, suitably connected to said probe, for generating electronic signals corresponding to surface ultrasonic wave reflections having an amplitude within at least one set of predetermined upper and lower thresholds.

33. A device according to claim 30, further comprising second electronic selection means, suitably connected to said probe, for generating electronic signals corresponding to surface ultrasonic wave reflections having significantly greater amplitude than the general level of background noise, wherein the time of flight of each of said wave reflections is within at least one set of predetermined upper and lower thresholds.

34. A device according to claim 32, further comprising visual and/or audio display means for displaying said electronic signals.

35. A device according to claim 33, further comprising visual and/or audio display means for displaying said electronic signals.

36. A device according to claim 30, further comprising microprocessor means operatively connected to said transducer for storing and/or analysing the electrical signals generated by said transducer corresponding to said ultrasonic surface wave reflections received at said transducer.

37. A device according to claim 36, wherein said microprocessor is accommodated in said handle.

38. A device according to claim 37, further comprising a suitable electronic display accommodated on said handle and operatively connected to said microprocessor.

39. A device according to claim 37, further comprising a rechargeable battery accommodated in said handle for providing the electrical needs of said device.

40. A device according to claim 36, further comprising means for providing electronic communication between said microprocessor and at least one electronic component external to said device.

41. A device according to claim 40, wherein said electronic component is an electronic computer.

42. A device according to claim 40, wherein said electronic component is a printer capable of printing data via said electronic computer and/or directly from said microprocessor.

43. A device according to claim 30, wherein said device is autoclavable.

44. A method for the detection of smooth surface lesions of a tooth crown surface, comprising the steps of:
 (i) providing a probe as claimed to claim 1;
 (ii) positioning said contact surface in substantial contact with said tooth crown surface at least at said intersection of said at least one longitudinal axis with said contact surface; wherein
 (iii) said probe can generate surface ultrasonic waves onto said tooth crown surface, said surface ultrasonic waves migrating along said tooth crown surface; and
 (iv) said probe receives at least some ultrasonic wave reflections produced at surface lesions present on said surface, thereby detecting said lesions.

45. A method for the detection of smooth surface lesions of a tooth crown surface, comprising the steps of:
 (i) providing a device as claimed to claim 30;
 (ii) positioning said contact surface in substantial contact with said tooth crown surface at least at said intersection of said at least one longitudinal axis with said contact surface; wherein
 (iii) said probe can generate surface ultrasonic waves onto said tooth crown surface, said surface ultrasonic waves migrating along said tooth crown surface; and
 (iv) said probe receives at least some ultrasonic wave reflections produced at surface lesions present on said surface, thereby detecting said lesions.

46. A method according to claim 45, wherein said ultrasonic surface wave reflections produced by a said lesion on said tooth crown surface are represented as a corresponding A-scan, comprising at least a primary echo and a secondary echo.

47. A method according to claim 46, wherein enamel caries lesions may be distinguished from dentinal caries lesions or tooth crown surface cracks, further comprising the steps of:
 (I) comparing the amplitude of the said primary echo with the range of primary echo amplitudes normally obtained for dentinal caries lesions and tooth crown surface cracks; and
 (II) identifying said lesion as an enamel caries lesion if said amplitude of said primary echo corresponding to said reflected ultrasonic surface waves is substantially lower than the said range of primary echo amplitudes normally obtained for dentinal caries lesions and tooth crown surface cracks; or
 (III) identifying said lesion as a dentinal caries lesion or a tooth crown surface crack if said amplitude of said primary echo corresponding to said reflected ultrasonic surface waves is substantially lower than the said range of primary echo amplitudes normally obtained for dentinal caries lesions and tooth crown surface cracks.

48. A method according to claim 46, wherein dentinal caries lesions may be distinguished from tooth crown surface cracks, further comprising the steps of:
 (I) determining the amplitude of the said primary echo and the RMS value of the said primary echo and the said secondary echo corresponding to said ultrasonic surface wave reflections, and incorporating the said primary echo amplitude and the said RMS value in a function F1 representing the said ultrasonic surface wave reflections
 (II) comparing the value of the function F1 obtained for said ultrasonic surface wave reflections in (I) with the range of values of the function F1 normally obtained for dentinal caries lesions and for tooth crown surface cracks; and
 (III) identifying said lesion as a dentinal caries lesion or as a tooth crown surface crack depending on whether the value of function F1 is within the range of values of the function F1 normally obtained for dentinal caries lesions or for tooth crown surface cracks, respectively.

49. A method according to claim 48, wherein said function F1 is the ratio of the amplitude of said primary echo to the RMS value of the said primary echo and the said secondary echo corresponding to said reflected ultrasonic surface waves.

50. A method according to claim 46, wherein secondary caries lesions at the gingival margin of an interproximal class II restoration may be distinguished from imperfections of said restoration, further comprising the steps of:
 (I) determining the amplitude of the said primary echo and the RMS value of the said primary echo and the said secondary echo corresponding to said ultrasonic surface wave reflections produced at said gingival margin, and incorporating the said primary echo amplitude and the said RMS value in a function F2 representing the said ultrasonic surface wave reflections;
 (II) comparing the value of the function F2 obtained for said ultrasonic surface wave reflections in (I) with the range of values of the function F2 normally obtained for secondary caries lesions and for class II restoration imperfections at the gingival margin; and
 (III) identifying a said secondary caries lesion or a class II restoration imperfection at the class II gingival margin depending on whether the value of function F2 is within the range of values of F2 normally for secondary caries lesions or for class II restoration imperfections, respectively.

51. A method according to claim 50, wherein said function F2 is the ratio of the amplitude of said primary echo to the said RMS value of the said primary echo and said secondary echo corresponding to said reflected ultrasonic surface waves.

* * * * *